United States Patent
Williams et al.

(10) Patent No.: US 9,931,216 B2
(45) Date of Patent: *Apr. 3, 2018

(54) ORTHOPAEDIC FEMORAL COMPONENT HAVING CONTROLLED CONDYLAR CURVATURE

(71) Applicant: DEPUY IRELAND UNLIMITED COMPANY, Cork (IE)

(72) Inventors: John L. Williams, Fort Wayne, IN (US); Said T. Gomaa, Fort Wayne, IN (US); John M. Armacost, Warsaw, IN (US)

(73) Assignee: DEPUY IRELAND UNLIMITED COMPANY, County Cork (IE)

( * ) Notice: Subject to any disclaimer, the term of this patent is extended or adjusted under 35 U.S.C. 154(b) by 0 days.

This patent is subject to a terminal disclaimer.

(21) Appl. No.: 14/983,079

(22) Filed: Dec. 29, 2015

(65) Prior Publication Data
US 2016/0184106 A1    Jun. 30, 2016

Related U.S. Application Data

(63) Continuation of application No. 14/453,371, filed on Aug. 6, 2014, now Pat. No. 9,220,601, which is a continuation of application No. 12/165,579, filed on Jun. 30, 2008, now Pat. No. 8,828,086.

(51) Int. Cl.
*A61F 2/38* (2006.01)

(52) U.S. Cl.
CPC .............. *A61F 2/3859* (2013.01); *A61F 2/38* (2013.01); *A61F 2/389* (2013.01); *A61F 2/3868* (2013.01); *A61F 2/3886* (2013.01); *A61F 2002/3863* (2013.01)

(58) Field of Classification Search
None
See application file for complete search history.

(56) References Cited

U.S. PATENT DOCUMENTS

| | | |
|---|---|---|
| 3,765,033 A | 10/1973 | Goldberg et al. |
| 3,840,905 A | 10/1974 | Deane |
| 3,852,045 A | 12/1974 | Wheeler |
| 3,855,638 A | 12/1974 | Pilliar |
| 3,869,731 A | 3/1975 | Waugh et al. |
| 4,081,866 A | 4/1978 | Upshaw et al. |
| 4,156,943 A | 6/1979 | Collier |
| 4,206,516 A | 6/1980 | Pilliar |

(Continued)

FOREIGN PATENT DOCUMENTS

| | | |
|---|---|---|
| CN | 1803106 A | 7/2006 |
| CN | 1872009 A | 12/2006 |

(Continued)

OTHER PUBLICATIONS

Carl Zeiss, Zeiss Surfcomm 5000—"Contour and Surface Measuring Machines", 2005, 16 pages.

(Continued)

*Primary Examiner* — David H Willse
*Assistant Examiner* — Javier Blanco
(74) *Attorney, Agent, or Firm* — Barnes & Thornburg LLP

(57) ABSTRACT

An orthopaedic knee prosthesis includes a femoral component having a condyle surface. The condyle surface is defined by one or more radii of curvatures, which are controlled to reduce or delay the onset of anterior translation of the femoral component relative to a tibial bearing.

15 Claims, 21 Drawing Sheets

(56) References Cited

U.S. PATENT DOCUMENTS

| | | |
|---|---|---|
| 4,209,861 A | 7/1980 | Walker et al. |
| 4,215,439 A | 8/1980 | Gold et al. |
| 4,249,270 A | 2/1981 | Bahler et al. |
| 4,257,129 A | 3/1981 | Volz |
| 4,262,368 A | 4/1981 | Lacey |
| 4,340,978 A | 7/1982 | Buechel et al. |
| 4,470,158 A | 9/1984 | Pappas et al. |
| 4,612,160 A | 9/1986 | Donlevy |
| 4,673,407 A | 6/1987 | Martin |
| 4,714,474 A | 12/1987 | Brooks, Jr. |
| 4,795,468 A | 1/1989 | Hodorek |
| 4,808,185 A | 2/1989 | Penenberg et al. |
| 4,822,362 A | 4/1989 | Walker |
| 4,838,891 A | 6/1989 | Branemark |
| 4,888,021 A | 12/1989 | Forte et al. |
| 4,938,769 A | 7/1990 | Shaw |
| 4,944,757 A | 7/1990 | Martinez |
| 4,944,760 A | 7/1990 | Kenna |
| 4,950,298 A | 8/1990 | Gustilo et al. |
| 4,963,152 A | 10/1990 | Hofmann et al. |
| 4,990,163 A | 2/1991 | Ducheyne |
| 5,007,933 A | 4/1991 | Sidebotham et al. |
| 5,011,496 A | 4/1991 | Forte et al. |
| 5,019,103 A | 5/1991 | Van Zile |
| 5,037,423 A | 8/1991 | Kenna |
| 5,071,438 A | 12/1991 | Jones et al. |
| 5,080,675 A | 1/1992 | Lawes |
| 5,104,410 A | 4/1992 | Chowdhary |
| 5,108,442 A | 4/1992 | Smith |
| 5,116,375 A | 5/1992 | Hofmann |
| 5,133,758 A | 7/1992 | Hollister |
| 5,147,405 A | 9/1992 | Van Zile et al. |
| 5,171,283 A | 12/1992 | Pappas |
| 5,201,766 A | 4/1993 | Georgette |
| 5,236,461 A | 8/1993 | Forte |
| 5,251,468 A | 10/1993 | Lin |
| 5,258,044 A | 11/1993 | Lee |
| 5,271,737 A | 12/1993 | Baldwin |
| 5,282,861 A | 2/1994 | Kaplan |
| 5,308,556 A | 5/1994 | Bagley |
| 5,309,639 A | 5/1994 | Lee |
| 5,326,361 A | 7/1994 | Hollister |
| 5,330,534 A | 7/1994 | Herrington et al. |
| 5,344,460 A | 9/1994 | Turanyi et al. |
| 5,344,461 A | 9/1994 | Phlipot |
| 5,344,494 A | 9/1994 | Davidson |
| 5,358,527 A | 10/1994 | Forte |
| 5,368,881 A | 11/1994 | Kelman |
| 5,370,699 A | 12/1994 | Hood et al. |
| 5,387,240 A | 2/1995 | Pottenger et al. |
| 5,395,401 A | 3/1995 | Bahler |
| 5,405,396 A | 4/1995 | Heldreth et al. |
| 5,413,604 A | 5/1995 | Hodge |
| 5,414,049 A | 5/1995 | Sun |
| 5,449,745 A | 9/1995 | Sun |
| 5,458,637 A | 10/1995 | Hayes |
| 5,480,446 A | 1/1996 | Goodfellow |
| 5,543,471 A | 8/1996 | Sun |
| 5,549,686 A | 8/1996 | Johnson et al. |
| 5,571,187 A | 11/1996 | Devanathan |
| 5,571,194 A | 11/1996 | Gabriel |
| 5,609,639 A | 3/1997 | Walker |
| 5,609,643 A | 3/1997 | Colleran et al. |
| 5,639,279 A | 6/1997 | Burkinshaw et al. |
| 5,650,485 A | 7/1997 | Sun |
| 5,658,333 A | 8/1997 | Kelman |
| 5,658,344 A | 8/1997 | Hurlburt |
| 5,681,354 A | 10/1997 | Eckhoff |
| 5,683,468 A | 11/1997 | Pappas |
| 5,702,463 A | 12/1997 | Pothier |
| 5,702,464 A | 12/1997 | Lackey et al. |
| 5,702,466 A | 12/1997 | Pappas et al. |
| 5,725,584 A | 3/1998 | Walker et al. |
| 5,728,748 A | 3/1998 | Sun |
| 5,732,469 A | 3/1998 | Hamamoto |
| 5,755,800 A | 5/1998 | O'Neil |
| 5,755,801 A | 5/1998 | Walker et al. |
| 5,755,803 A | 5/1998 | Haines et al. |
| 5,765,095 A | 6/1998 | Flak |
| 5,766,257 A | 6/1998 | Goodman et al. |
| 5,776,201 A | 7/1998 | Colleran et al. |
| 5,800,552 A | 9/1998 | Forte |
| 5,811,543 A | 9/1998 | Hao et al. |
| 5,824,096 A | 10/1998 | Pappas et al. |
| 5,824,102 A | 10/1998 | Buscayret |
| 5,824,103 A | 10/1998 | Williams |
| 5,871,543 A | 2/1999 | Hofmann |
| 5,871,545 A | 2/1999 | Goodfellow |
| 5,871,546 A | 2/1999 | Colleran et al. |
| 5,879,394 A | 3/1999 | Ashby |
| 5,879,400 A | 3/1999 | Merrill |
| 5,906,644 A | 5/1999 | Powell |
| 5,951,603 A | 9/1999 | O'Neil et al. |
| 5,957,979 A | 9/1999 | Beckman |
| 5,964,808 A | 10/1999 | Blaha |
| 5,976,147 A | 11/1999 | LaSalle et al. |
| 5,984,969 A | 11/1999 | Matthews |
| 5,989,027 A | 11/1999 | Wagner |
| 5,997,577 A | 12/1999 | Herrington et al. |
| 6,005,018 A | 12/1999 | Cicierega |
| 6,010,534 A | 1/2000 | O'Neil et al. |
| 6,013,103 A | 1/2000 | Kaufman et al. |
| 6,017,975 A | 1/2000 | Saum |
| 6,039,764 A | 3/2000 | Pottenger et al. |
| 6,042,780 A | 3/2000 | Huang |
| 6,053,945 A | 4/2000 | O'Neil et al. |
| 6,059,949 A | 5/2000 | Gal Or |
| 6,068,658 A | 5/2000 | Insall |
| 6,080,195 A | 6/2000 | Colleran et al. |
| 6,090,144 A | 7/2000 | Letot |
| 6,123,728 A | 9/2000 | Brosnahan |
| 6,123,896 A | 9/2000 | Meeks, III |
| 6,126,692 A | 10/2000 | Robie et al. |
| 6,135,857 A | 10/2000 | Shaw |
| 6,139,581 A | 10/2000 | Engh et al. |
| 6,152,960 A | 11/2000 | Pappas |
| 6,162,254 A | 12/2000 | Timoteo |
| 6,174,934 B1 | 1/2001 | Sun |
| 6,206,926 B1 | 3/2001 | Pappas |
| 6,210,444 B1 | 4/2001 | Webster |
| 6,210,445 B1 | 4/2001 | Zawadzki |
| 6,217,618 B1 | 4/2001 | Hileman |
| 6,228,900 B1 | 5/2001 | Shen |
| 6,238,434 B1 | 5/2001 | Pappas |
| 6,242,507 B1 | 6/2001 | Saum |
| 6,245,276 B1 | 6/2001 | McNulty |
| 6,258,127 B1 | 7/2001 | Schmotzer |
| 6,264,697 B1 | 7/2001 | Walker |
| 6,280,476 B1 | 8/2001 | Metzger |
| 6,281,264 B1 | 8/2001 | Salovey |
| 6,299,646 B1 | 10/2001 | Chambat et al. |
| 6,316,158 B1 | 11/2001 | Saum |
| 6,319,283 B1 | 11/2001 | Insall |
| 6,325,828 B1 | 12/2001 | Dennis et al. |
| 6,344,059 B1 | 2/2002 | Krakovits et al. |
| 6,361,564 B1 | 3/2002 | Marceaux |
| 6,372,814 B1 | 4/2002 | Sun |
| 6,379,388 B1 | 4/2002 | Ensign et al. |
| 6,428,577 B1 | 8/2002 | Evans et al. |
| 6,485,519 B2 | 11/2002 | Meyers et al. |
| 6,491,726 B2 | 12/2002 | Pappas |
| 6,494,914 B2 | 12/2002 | Brown et al. |
| 6,503,280 B2 | 1/2003 | Repicci |
| 6,506,215 B1 | 1/2003 | Letot |
| 6,506,216 B1 | 1/2003 | McCue |
| 6,524,522 B2 | 2/2003 | Vaidyanathan |
| 6,540,787 B2 | 4/2003 | Biegun et al. |
| 6,558,426 B1 | 5/2003 | Masini |
| 6,569,202 B2 | 5/2003 | Whiteside |
| 6,582,469 B1 | 6/2003 | Tornier |
| 6,582,470 B1 | 6/2003 | Lee |
| 6,589,283 B1 | 7/2003 | Metzger et al. |
| 6,592,787 B2 | 7/2003 | Pickrell |
| 6,620,198 B2 | 9/2003 | Burstein et al. |

(56) References Cited

U.S. PATENT DOCUMENTS

| | | |
|---|---|---|
| 6,623,526 B1 | 9/2003 | Lloyd |
| 6,645,251 B2 | 11/2003 | Salehi et al. |
| 6,660,039 B1 | 12/2003 | Evans et al. |
| 6,660,224 B2 | 12/2003 | Lefebvre |
| 6,664,308 B2 | 12/2003 | Sun |
| 6,702,821 B2 | 3/2004 | Bonutti |
| 6,719,800 B2 | 4/2004 | Meyers et al. |
| 6,726,724 B2 | 4/2004 | Repicci |
| 6,730,128 B2 | 5/2004 | Burstein |
| 6,764,516 B2 | 7/2004 | Pappas |
| 6,770,078 B2 | 8/2004 | Bonutti |
| 6,770,099 B2 | 8/2004 | Andriacchi et al. |
| 6,773,461 B2 | 8/2004 | Meyers et al. |
| 6,797,005 B2 | 9/2004 | Pappas |
| 6,818,020 B2 | 11/2004 | Sun |
| 6,846,327 B2 | 1/2005 | Khandkar |
| 6,846,329 B2 | 1/2005 | McMinn |
| 6,849,230 B1 | 2/2005 | Feichtinger |
| 6,852,272 B2 | 2/2005 | Artz |
| 6,869,448 B2 | 3/2005 | Tuke et al. |
| 6,916,340 B2 | 7/2005 | Metzger et al. |
| 6,923,832 B1 | 8/2005 | Sharkey |
| 6,942,670 B2 | 9/2005 | Heldreth et al. |
| 6,972,039 B2 | 12/2005 | Metzger et al. |
| 6,986,791 B1 | 1/2006 | Metzger |
| 7,025,788 B2 | 4/2006 | Metzger et al. |
| 7,048,741 B2 | 5/2006 | Swanson |
| 7,066,963 B2 | 6/2006 | Naegerl |
| 7,070,622 B1 | 7/2006 | Brown |
| 7,081,137 B1 | 7/2006 | Servidio |
| 7,094,259 B2 | 8/2006 | Tarabichi |
| 7,101,401 B2 | 9/2006 | Brack |
| 7,104,996 B2 | 9/2006 | Bonutti |
| 7,147,819 B2 | 12/2006 | Bram |
| 7,175,665 B2 | 2/2007 | German |
| 7,255,715 B2 | 8/2007 | Metzger |
| 7,261,740 B2 | 8/2007 | Tuttle et al. |
| 7,297,164 B2 | 11/2007 | Johnson et al. |
| 7,326,252 B2 | 2/2008 | Otto et al. |
| 7,341,602 B2 | 3/2008 | Fell et al. |
| 7,344,460 B2 | 3/2008 | Gait |
| 7,357,817 B2 | 4/2008 | D'Alessio, II |
| 7,422,605 B2 | 9/2008 | Burseein et al. |
| 7,510,557 B1 | 3/2009 | Bonutti |
| 7,527,650 B2 | 5/2009 | Johnson et al. |
| 7,572,292 B2 | 8/2009 | Crabtree et al. |
| 7,578,850 B2 | 8/2009 | Kuczynski et al. |
| 7,608,079 B1 | 10/2009 | Blackwell et al. |
| 7,611,519 B2 | 11/2009 | Lefevre et al. |
| 7,615,054 B1 | 11/2009 | Bonutti |
| 7,618,462 B2 | 11/2009 | Ek |
| 7,628,818 B2 | 12/2009 | Hazebrouck et al. |
| 7,635,390 B1 | 12/2009 | Bonutti |
| 7,658,767 B2 | 2/2010 | Wyss |
| 7,678,151 B2 | 3/2010 | Ek |
| 7,678,152 B2 | 3/2010 | Suguro et al. |
| 7,708,740 B1 | 5/2010 | Bonutti |
| 7,708,741 B1 | 5/2010 | Bonutti |
| 7,740,662 B2 | 6/2010 | Barnett et al. |
| 7,749,229 B1 | 7/2010 | Bonutti |
| 7,753,960 B2 | 7/2010 | Cipolletti et al. |
| 7,771,484 B2 | 8/2010 | Campbell |
| 7,776,044 B2 | 8/2010 | Pendleton |
| 7,806,896 B1 | 10/2010 | Bonutti |
| 7,806,897 B1 | 10/2010 | Bonutti |
| 7,837,736 B2 | 11/2010 | Bonutti |
| 7,842,093 B2 | 11/2010 | Peters et al. |
| 7,875,081 B2 | 1/2011 | Lipman et al. |
| 7,922,771 B2 | 4/2011 | Otto et al. |
| 8,206,451 B2 | 6/2012 | Wyss et al. |
| 8,236,061 B2 | 8/2012 | Heldreth et al. |
| 2002/0138150 A1 | 9/2002 | Leclercq |
| 2003/0009232 A1 | 1/2003 | Metzger et al. |
| 2003/0035747 A1 | 2/2003 | Anderson |
| 2003/0044301 A1 | 3/2003 | Lefebvre |
| 2003/0075013 A1 | 4/2003 | Grohowski |
| 2003/0139817 A1 | 7/2003 | Tuke |
| 2003/0153981 A1 | 8/2003 | Wang |
| 2003/0171820 A1 | 9/2003 | Wilshaw |
| 2003/0199985 A1 | 10/2003 | Masini |
| 2003/0212161 A1 | 11/2003 | McKellop |
| 2003/0225456 A1 | 12/2003 | Ek |
| 2004/0015770 A1 | 1/2004 | Kimoto |
| 2004/0039450 A1 | 2/2004 | Griner et al. |
| 2004/0167633 A1 | 8/2004 | Wen |
| 2004/0186583 A1 | 9/2004 | Keller |
| 2004/0215345 A1 | 10/2004 | Perrone |
| 2004/0243245 A1 | 12/2004 | Plumet et al. |
| 2005/0021147 A1 | 1/2005 | Tarabichi |
| 2005/0055102 A1 | 3/2005 | Tornier |
| 2005/0059750 A1 | 3/2005 | Sun |
| 2005/0069629 A1 | 3/2005 | Becker |
| 2005/0096747 A1 | 5/2005 | Tuttle et al. |
| 2005/0100578 A1 | 5/2005 | Schmid |
| 2005/0123672 A1 | 6/2005 | Justin |
| 2005/0143832 A1 | 6/2005 | Carson |
| 2005/0203631 A1 | 9/2005 | Daniels |
| 2005/0209701 A1 | 9/2005 | Suguro et al. |
| 2005/0209702 A1 | 9/2005 | Todd |
| 2005/0249625 A1 | 11/2005 | Bram |
| 2005/0278035 A1 | 12/2005 | Wyss |
| 2006/0002810 A1 | 1/2006 | Grohowski |
| 2006/0015185 A1 | 1/2006 | Chambat et al. |
| 2006/0036329 A1 | 2/2006 | Webster |
| 2006/0052875 A1 | 3/2006 | Bernero |
| 2006/0100714 A1 | 5/2006 | Ensign |
| 2006/0178749 A1 | 8/2006 | Pendleton et al. |
| 2006/0195195 A1 | 8/2006 | Burstein |
| 2006/0228247 A1 | 10/2006 | Grohowski |
| 2006/0231402 A1 | 10/2006 | Clasen |
| 2006/0241781 A1 | 10/2006 | Brown |
| 2006/0257358 A1 | 11/2006 | Wen |
| 2006/0271191 A1 | 11/2006 | Hermansson |
| 2006/0289388 A1 | 12/2006 | Yang |
| 2007/0061014 A1 | 3/2007 | Naegerl |
| 2007/0073409 A1 | 3/2007 | Cooney |
| 2007/0078521 A1 | 4/2007 | Overholser |
| 2007/0100463 A1 | 5/2007 | Aram |
| 2007/0129809 A1 | 6/2007 | Meridew |
| 2007/0135926 A1 | 6/2007 | Walker |
| 2007/0173948 A1 | 7/2007 | Meridew |
| 2007/0196230 A1 | 8/2007 | Hamman |
| 2007/0203582 A1 | 8/2007 | Campbell |
| 2007/0219639 A1 | 9/2007 | Otto et al. |
| 2007/0293647 A1 | 12/2007 | McKellop |
| 2008/0004708 A1 | 1/2008 | Wyss |
| 2008/0021566 A1 | 1/2008 | Peters et al. |
| 2008/0091272 A1 | 4/2008 | Aram |
| 2008/0097616 A1 | 4/2008 | Meyers et al. |
| 2008/0114462 A1 | 5/2008 | Guidera et al. |
| 2008/0114464 A1 | 5/2008 | Barnett et al. |
| 2008/0119940 A1 | 5/2008 | Otto et al. |
| 2008/0161927 A1 | 7/2008 | Savage |
| 2008/0195108 A1 | 8/2008 | Bhatnagar et al. |
| 2008/0199720 A1 | 8/2008 | Liu |
| 2008/0206297 A1 | 8/2008 | Roeder |
| 2008/0269596 A1 | 10/2008 | Revie et al. |
| 2009/0043396 A1 | 2/2009 | Komistek |
| 2009/0048680 A1 | 2/2009 | Naegerl |
| 2009/0082873 A1 | 3/2009 | Hazebrouck |
| 2009/0084491 A1 | 4/2009 | Uthgenannt |
| 2009/0088859 A1 | 4/2009 | Hazebrouck et al. |
| 2009/0125114 A1 | 5/2009 | May et al. |
| 2009/0192610 A1 | 7/2009 | Case |
| 2009/0265012 A1 | 10/2009 | Engh et al. |
| 2009/0265013 A1 | 10/2009 | Mendell |
| 2009/0292365 A1 | 11/2009 | Smith |
| 2009/0295035 A1 | 12/2009 | Evans |
| 2009/0306785 A1 | 12/2009 | Farrar et al. |
| 2009/0319047 A1 | 12/2009 | Walker |
| 2009/0326663 A1 | 12/2009 | Dun |
| 2009/0326664 A1 | 12/2009 | Wagner et al. |
| 2009/0326665 A1 | 12/2009 | Wyss et al. |
| 2009/0326666 A1 | 12/2009 | Wyss et al. |

(56) References Cited

U.S. PATENT DOCUMENTS

| | | |
|---|---|---|
| 2009/0326667 A1 | 12/2009 | Williams et al. |
| 2009/0326674 A1 | 12/2009 | Liu |
| 2010/0016979 A1 | 1/2010 | Wyss et al. |
| 2010/0036499 A1 | 2/2010 | Pinskerova |
| 2010/0036500 A1 | 2/2010 | Heldreth |
| 2010/0042224 A1 | 2/2010 | Otto et al. |
| 2010/0042225 A1 | 2/2010 | Shur |
| 2010/0063594 A1 | 3/2010 | Hazebrouck |
| 2010/0070045 A1 | 3/2010 | Ek |
| 2010/0076563 A1 | 3/2010 | Otto et al. |
| 2010/0076564 A1 | 3/2010 | Schilling et al. |
| 2010/0094429 A1 | 4/2010 | Otto |
| 2010/0098574 A1 | 4/2010 | Liu |
| 2010/0100189 A1 | 4/2010 | Metzger |
| 2010/0100190 A1 | 4/2010 | May et al. |
| 2010/0100191 A1 | 4/2010 | May et al. |
| 2010/0125337 A1 | 5/2010 | Grecco et al. |
| 2010/0161067 A1 | 6/2010 | Saleh et al. |
| 2010/0191341 A1 | 7/2010 | Byrd |
| 2010/0222890 A1 | 9/2010 | Barnett |
| 2010/0286788 A1 | 11/2010 | Komistek |
| 2010/0292804 A1 | 11/2010 | Samuelson |
| 2010/0305710 A1 | 12/2010 | Metzger |
| 2010/0312350 A1 | 12/2010 | Bonutti |
| 2011/0029090 A1 | 2/2011 | Zannis |
| 2011/0029092 A1 | 2/2011 | Deruntz |
| 2011/0035017 A1 | 2/2011 | Deffenbaugh |
| 2011/0035018 A1 | 2/2011 | Deffenbaugh |
| 2011/0106268 A1 | 5/2011 | Deffenbaugh |
| 2011/0118847 A1 | 5/2011 | Lipman et al. |
| 2011/0125280 A1 | 5/2011 | Otto et al. |
| 2011/0153026 A1 | 6/2011 | Heggendorn et al. |
| 2012/0239158 A1 | 9/2012 | Wagner et al. |
| 2012/0259417 A1 | 10/2012 | Wyss et al. |
| 2012/0271428 A1 | 10/2012 | Heldreth et al. |
| 2012/0296437 A1 | 11/2012 | Wyss et al. |
| 2013/0006372 A1 | 1/2013 | Wyss et al. |
| 2013/0006373 A1 | 1/2013 | Wyss et al. |

FOREIGN PATENT DOCUMENTS

| | | |
|---|---|---|
| DE | 4308563 A1 | 9/1994 |
| DE | 19529824 A1 | 2/1997 |
| EP | 495340 A1 | 7/1992 |
| EP | 636352 A2 | 2/1995 |
| EP | 732091 A2 | 9/1996 |
| EP | 634156 B1 | 5/1999 |
| EP | 1129676 | 9/2001 |
| EP | 636352 B1 | 1/2002 |
| EP | 765645 B1 | 8/2003 |
| EP | 1374805 | 1/2004 |
| EP | 1421918 A1 | 5/2004 |
| EP | 1440675 | 7/2004 |
| EP | 1470801 | 10/2004 |
| EP | 732092 B1 | 2/2005 |
| EP | 1518521 A2 | 3/2005 |
| EP | 1226799 B1 | 5/2005 |
| EP | 1591082 A2 | 11/2005 |
| EP | 1779812 A1 | 5/2007 |
| EP | 1923079 A1 | 5/2008 |
| FR | 2417971 | 2/1979 |
| FR | 2653992 A1 | 5/1991 |
| FR | 2780636 A1 | 1/2000 |
| FR | 2787012 A1 | 6/2000 |
| FR | 2809302 A1 | 11/2001 |
| FR | 2835178 A1 | 8/2003 |
| GB | 1065354 A | 4/1967 |
| GB | 2293109 A | 3/1996 |
| GB | 2335145 A | 9/1999 |
| JP | 56-083343 | 7/1981 |
| JP | 62205201 | 9/1987 |
| JP | 8500992 T | 2/1996 |
| JP | 08-503407 | 4/1996 |
| JP | 8224263 | 9/1996 |
| JP | 2002291779 A | 10/2002 |
| JP | 2004167255 | 6/2004 |
| JP | 2006015133 A | 1/2006 |
| WO | 7900739 | 10/1979 |
| WO | 8906947 | 8/1989 |
| WO | 90014806 A1 | 12/1990 |
| WO | 1990014806 A1 | 12/1990 |
| WO | 9623458 | 8/1996 |
| WO | 9624311 | 8/1996 |
| WO | 9624312 | 8/1996 |
| WO | 9846171 | 10/1998 |
| WO | 9927872 | 6/1999 |
| WO | 99066864 A1 | 12/1999 |
| WO | 209624 A1 | 2/2002 |
| WO | 03039609 A1 | 5/2003 |
| WO | 03101647 A2 | 12/2003 |
| WO | 2004058108 A1 | 7/2004 |
| WO | 2004069104 | 8/2004 |
| WO | 05009489 A2 | 2/2005 |
| WO | 05009729 A2 | 2/2005 |
| WO | 5072657 A1 | 8/2005 |
| WO | 06014294 A1 | 2/2006 |
| WO | 06130350 A2 | 12/2006 |
| WO | 2007106172 A | 9/2007 |
| WO | 2007108804 A1 | 9/2007 |
| WO | 2007119173 | 10/2007 |
| WO | 08100784 A2 | 8/2008 |
| WO | 09046212 A2 | 4/2009 |
| WO | 09128943 A2 | 10/2009 |

OTHER PUBLICATIONS

Zimmer Nexgen Trabecular Metal Tibial Tray, The Best Thing Next to Bone, 97-5954-001-00, 2007, 4 pages.

European Search Report for European Patent Application No. 08164944.4-2310-2042131, dated Mar. 16, 2009, 12 pgs.

European Search Report for European Patent Application No. 08253140.1-2310, dated Dec. 23, 2008, 7 pgs.

European Search Report for European Patent Application No. 11150648.1-2310, dated Apr. 7, 2011, 4 pages.

Zimmer, Trabecular Metal Monoblock Tibial Components, an Optimal Combination of Material and Design, www.zimmer.com, 2009, 3 pages.

Biomet, Vanguard Mono-Lock Tibial System, Patented Convertible Tibial Bearing Technology, 2009, 2 Pages.

DePuy Inc., "AMK Total Knee System Product Brochure", 1996, 8 pages.

DePuy Knees International, "Sigma CR Porocoat®," 1 page, Publication date prior to Jun. 30, 2007.

DePuy Orthopaedics, Inc., "AMK Total Knee System Legent II Surgical Techinque", 1998, 30 pages.

DePuy Orthopaedics, Inc., "Sigma Fixed Bearing Knees—Function with Wear Resistance", 2010, 0612-65-508 (Rev. 1) 20 pages.

European Search Report for European Patent Application No. 06739287.8-2310, dated Mar. 16, 2010, 3 pages.

European Search Report for European Patent Application No. 09164478.1-2310, dated Oct. 20, 2009, 6 pages.

European Search Report for European Patent Application No. 09164478.1-2310, dated Apr. 28, 2010, 12 pages.

European Search Report for European Patent Application No. 10162138.1, dated Aug. 30, 2010, 7 pages.

Japanese Search Report for Japanese Patent Application No. 2009-501393, dated Oct. 26, 2010, 5 pages.

PCT Notification Concerning Transmittal of International Prel. Report for Corresponding International App. No. PCT/US2006/010431, dated Jun. 5, 2007, 89 Pages.

Procedure, References Guide for Use with P.F.C. Sigma Knee Systems, 1998, 8 pages.

Signus Medizintechnik, "Peek-Optima®, The Polymer for Implants, Technical Information for the Medical Professional", 7 pages, Publication date prior to Jun. 30, 2007.

Effects of Coronal Plane Conformity on Tibial Loading in TKA: A Comparison of AGC Flat Versus Conforming Articulations, Brent, et al, Orthopaedic Surgery, Surgical Technology International, XVIII, 6 pages, Publication date prior to Jun. 30, 2007.

(56) References Cited

OTHER PUBLICATIONS

DePuy PFC Sigma RP, "PFC Sigma Knee System with Rotating Platform Technical Monograph", 1999, 0611-29-050 (Rev. 3), 70 pages.
The Effects of Conformity and Load in Total Knee Replacement, Kuster, et al, Clinical Orthopaedics and Related Research No. 375, Jun. 2000.
Japanese Search Report, Japanese Patent Application No. 2009-153350, dated Jun. 18, 2013, 4 pages.
European Search Report for European Patent Application No. 09164245.4-2310, dated Oct. 15, 2009, 5 pages.
Shaw et al., "The Longitudinal Axis of the Knee and the Role of the Cruciate Ligaments in Controlling Transverse Rotation", J.Bone Joint Surg. Am. 1974:56:1603-1609, 8 Pages.
Kurosawa, et al., "Geometry and Motion of the Knee for Implant and Orthotic Design", The Journal of Biomechanics 18 (1985), pp. 487-499, 12 Pages.
Barnes, C.L., et al, "Kneeling Is Safe for Patients Implanted With Medical-Pivot Total Knee Arthoplasty Designs, Journal of Arthoplasty", vol. 00, No. 0 2010, 1-6, 6 Pages.
Blaha, et al., "Kinematics of the Human Knee Using an Open Chain Cadaver Model", Clinical Orthopaedics and Related Research, vol. 410 (2003); 25-34, 10 Pages.
Dennis, et al. "A Multi-Center Analysis of Axial Femorotibial Rotation After Total Knee Arthoplasty", Clinical Orthopaedics 428 (2004); 180-189, 10 Pages.
Fan, Cheng-Yu, et al, "Primitive Results After Medical-Pivot Knee Arthroplasties: A Minimum 5 Year Follow-Up Study", The Journal of Arthroplasty, vol. 25, No. 3 2010, 492-496, 5 Pages.
Freeman, M.A.R., et al., "The Movement of the Normal Tibio-Femoral Joint", The Journal of Biomechanics 38 (2005) (2), pp. 197-208, 12 Pgs.
Fuller, et al., "A Comparison of Lower-Extremity Skeletal Kinematics Measured Using Skin and Pin-Mounted Markers", Human Movement Science 16 (1997) 219-242, 24 Pages.
Hill, et al., "Tibiofemoral Movement 2: The Loaded and Unloaded Living Knee Studied by MRI" The Journal of Bone & Joint Surgery, vol. 82-B, No. 8 (Nov. 2000), 1196-1198, 3 Pages.
Karachalios, et al., "A Mid-Term Clinical Outcome Study of the Advance Medial Pivot Knee Arthroplasty", www.sciencedirect.come, The Knee 16 (2009); 484-488, 5 Pages.
Komistek, et al., "In Vivo Flouroscopic Analysis of the Normal Human Knee", Clinical Orthopaedics 410 (2003): 69-81, 13 Pages.
Komistek, et al., "In Vivo Polyethylene Bearing Mobility Is Maintained in Posterior Stabilized Total Knee Arthroplasty", Clinical Orthopaedics 428 (2004): 207-213, 7 Pages.
Koo, et al., "The Knee Joint Center of Rotation Is Predominantly on the Lateral Side During Normal Walking", Journal of Biomechanics, vol. 41 (2008): 1269-1273, 5 Pages.
Mannan, et al., "The Medical Rotation Total Knee Replacement: A Clinical and Radiological Review at a Mean Follow-Up of Six Years", The Journal of Bone and Joint Surgery, vol. 91-B, No. 6 (Jun. 2009): 750-756, 7 Pages.
Moonot, et al., "Correlation Between the Oxford Knee and American Knee Society Scores at Mid-Term Follow-Up", The Journal of Knee Surgery, vol. 22, No. 3 (Jul. 2009), 226-230, 5 Pages.
Murphy, Michael Charles, "Geometry and the Kinematics of the Normal Human Knee", Submitted to Masachusetts Institute of Technology (1990), 379 Pages.
Nakagawa, et al., "Tibiofemoral Movement 3: Full Flexion of the Normal Human Knee", J.Bone Joint Surg. Am, vol. 82-B, No. 8 (2000). 1199-1200, 2 Pages.
Omori, et al., "The Effect of Geometry of the Tibial Polyethylene Insert on the Tibiofemoral Contact Kinematics in Advance Medical Pivot Total Knee Arthroplasty", The Journal of Orthopaedics Science (2009), 14:754-760, 7 Pages.
Shakespeare, et al., "Flexion After Total Knee Replacement. A Comparison Between the Medical Pivot Knee and a Posterior Stabilised Knee", www.sciencedirect.com, The Knee 13 (2006): 371-372, 3 Pages.
Walker, et al., "Motion of a Mobile Bearing Knee Allowing Translation of Rotation", Journal of Arthroplasty 17 (2002): 11-19, 9 Pages.
European Patent Office, Search Report for App. No. 09164479.9-2310, dated Nov. 4, 2009, 6 pages.
2nd Int'l Johnson-Elloy Knee Meeting, Mar. 1987, 9 pages.
Operative Technique, Johnson Elloy Knee System, Chas F. Thackray, Ltd., 1988, 34 pgs.
Operative Technique the Turning Point, Accord, The Johnson/Elloy Concept, Chas FL Thackray Ltd, 32 pages, Publication date prior to Jun. 30, 2007.
Restoration of Soft Tissue Stability, Johnson, et al., Chas. F. Thackray, Ltd., 21 pages, Publication date prior to Jun. 30, 2007.
The Accuracy of Intramedullary Alignment in Total Knee Replacement, Elloy, et al, Chas F. Thackray Ltd, 12 pages, Publication date prior to Jun. 30, 2007.
The Turning Point, Accord, The Johnson Elloy Concept, Chas F. Thackray Ltd, 20 pages, Publication date prior to Jun. 30, 2007.
Prosthesis and Instrumentation the Turning Point, Accord, The Johnson/Elloy Concept, Chas F. Thackray Ltd, 8 pages, Publication date prior to Jun. 30, 2007.
Five to Eight Year Results of the Johnson/Elloy (Accord) Total Knee Arthroplasty, Johnson et al, The Journal of Arthroplasty, vol. 8, No. 1, Feb. 1993, 6 pages.
Factors Affecting the Range of Movement of Total Knee Arthroplasty, Harvey et al, The Journal of Bone and Joint Surgery, vol. 75-B, No. 6, Nov. 1993, 6 pages.
Advice Notice (NI) 2000/03, Defect & Investigation Centre, Mar. 13, 2000, 3 pages.
The Johnson Elloy (Accord) Total Knee Replacement, Norton et al, The Journal of Bone and Joint Surgery (BR), vol. 84, No. 6, Aug. 2002, 4 pages.
Midvatus Approach in Total Knee Arthroplasty, a Description and a Cadaveric Study Determining the Distance of the Popliteal Artery From the Patellar Margin of the Incision, Cooper et al., The Journal of Arthoplasty, vol. 14 No. 4, 1999, 4 Pages.
European Search Report for European Application No. 10174439.9-1526; dated Dec. 20, 2010, 4 pages.
European Search Report for European Patent Application No. 09164160.5-1526, dated Jan. 4, 2010, 4 pages.
European Search Report for European Patent Application No. 09164228.0-1526, dated Feb. 2, 2010, 6 pages.
European Search Report for European Patent Application No. 09164235.5-1526, dated Dec. 22, 2009, 6 pages.

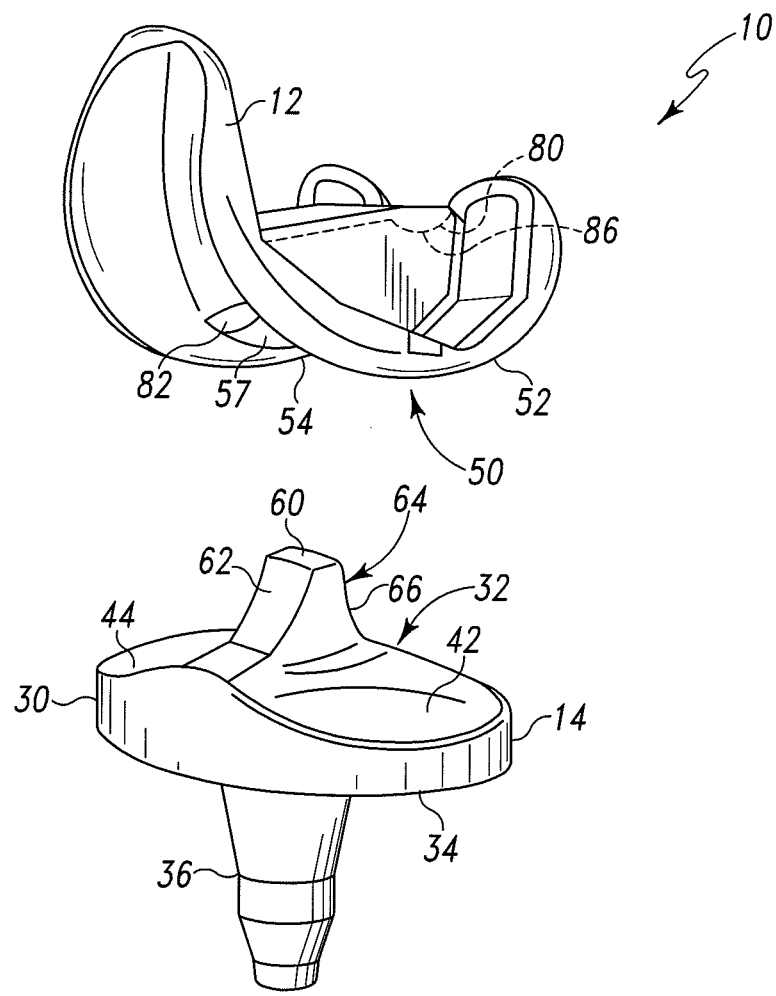
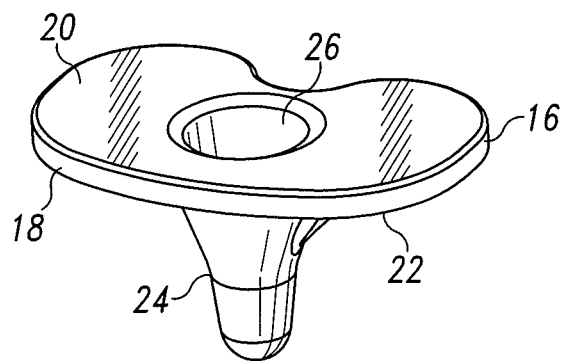

ORTHOPAEDIC FEMORAL COMPONENT HAVING CONTROLLED CONDYLAR CURVATURE

This application is a continuation of U.S. Utility patent application Ser. No. 14/453,371 entitled "ORTHOPAEDIC FEMORAL COMPONENT HAVING CONTROLLED CONDYLAR CURVATURE," which is a continuation of U.S. Utility patent application Ser. No. 12/165,579, now U.S. Pat. No. 8,828,086 entitled "ORTHOPAEDIC FEMORAL COMPONENT HAVING CONTROLLED CONDYLAR CURVATURE," both of which are expressly incorporated herein by reference.

CROSS-REFERENCE TO RELATED U.S. PATENT APPLICATION

Cross-reference is made to U.S. Utility patent application Ser. No. 12/165,574 entitled "Posterior Cruciate-Retaining Orthopaedic Knee Prosthesis Having Controlled Condylar Curvature" by Christel M. Wagner, which was filed on Jun. 30, 2008 and is now issued as U.S. Pat. No. 8,192,498; to U.S. Utility patent application Ser. No. 12/165,575 entitled "Posterior Stabilized Orthopaedic Knee Prosthesis Having Controlled Condylar Curvature" by Joseph G. Wyss, which was filed on Jun. 30, 2008 and is now issued as U.S. Pat. No. 8,187,335; and to U.S. Utility patent application Ser. No. 12/165,582 entitled "Posterior Stabilized Orthopaedic Prosthesis" by Joseph G. Wyss, which was filed on Jun. 30, 2008 and is now issued as U.S. Pat. No. 8,206,451; and to U.S. Utility patent application Ser. No. 12/488,107 entitled "Orthopaedic Knee Prosthesis Having Controlled Condylar Curvature" by Mark A. Heldreth, which was filed on Jun. 19, 2009 and is now issued as U.S. Pat. No. 8,236,061; the entirety of each of which is incorporated herein by reference.

TECHNICAL FIELD

The present disclosure relates generally to orthopaedic prostheses, and particularly to orthopaedic prostheses for use in knee replacement surgery.

BACKGROUND

Joint arthroplasty is a well-known surgical procedure by which a diseased and/or damaged natural joint is replaced by a prosthetic joint. A typical knee prosthesis includes a tibial tray, a femoral component, and a polymer insert or bearing positioned between the tibial tray and the femoral component. Depending on the severity of the damage to the patient's joint, orthopaedic prostheses of varying mobility may be used. For example, the knee prosthesis may include a "fixed" tibial bearing in cases wherein it is desirable to limit the movement of the knee prosthesis, such as when significant soft tissue damage or loss is present. Alternatively, the knee prosthesis may include a "mobile" tibial bearing in cases wherein a greater degree of freedom of movement is desired. Additionally, the knee prosthesis may be a total knee prosthesis designed to replace the femoral-tibial interface of both condyles of the patient's femur or a uni-compartmental (or uni-condylar) knee prosthesis designed to replace the femoral-tibial interface of a single condyle of the patient's femur.

The type of orthopedic knee prosthesis used to replace a patient's natural knee may also depend on whether the patient's posterior cruciate ligament is retained or sacrificed (i.e., removed) during surgery. For example, if the patient's posterior cruciate ligament is damaged, diseased, and/or otherwise removed during surgery, a posterior stabilized knee prosthesis may be used to provide additional support and/or control at later degrees of flexion. Alternatively, if the posterior cruciate ligament is intact, a cruciate retaining knee prosthesis may be used.

Typical orthopaedic knee prostheses are generally designed to duplicate the natural movement of the patient's joint. As the knee is flexed and extended, the femoral and tibial components articulate and undergo combinations of relative anterior-posterior motion and relative internal-external rotation. However, the patient's surrounding soft tissue also impacts the kinematics and stability of the orthopaedic knee prosthesis throughout the joint's range of motion. That is, forces exerted on the orthopaedic components by the patient's soft tissue may cause unwanted or undesirable motion of the orthopaedic knee prosthesis. For example, the orthopaedic knee prosthesis may exhibit an amount of unnatural (paradoxical) anterior translation as the femoral component is moved through the range of flexion.

In a typical orthopaedic knee prosthesis, paradoxical anterior translation may occur at nearly any degree of flexion, but particularly at mid to late degrees of flexion. Paradoxical anterior translation can be generally defined as an abnormal relative movement of a femoral component on a tibial bearing wherein the contact "point" between the femoral component and the tibial bearing "slides" anteriorly with respect to the tibial bearing. This paradoxical anterior translation may result in loss of joint stability, accelerated wear, abnormal knee kinematics, and/or cause the patient to experience a sensation of instability during some activities.

SUMMARY

According to one aspect, an orthopaedic knee prosthesis may include a femoral component and a tibial bearing. The femoral component may include a condyle surface that is curved in the sagittal plane. The tibial bearing may include a bearing surface configured to articulate with the condyle surface of the femoral component. In some embodiments, the condyle surface of the femoral component may contact the bearing surface at a first contact point on the condyle surface at a first degree of flexion equal to about 0 degrees. The condyle surface may also contact the bearing surface at a second contact point on the condyle surface at a second degree of flexion. The second degree of flexion may be greater than the first degree of flexion. For example, the second degree of flexion may be in the range of about 10 degrees to about 100 degrees. In one particular embodiment, the second degree of flexion is about 30 degrees.

The condyle surface in the sagittal plane may have a first radius of curvature at the first contact point and a second radius of curvature at the second contact point. The second radius of curvature may be greater than the first radius of curvature by at least 0.5 millimeters. For example, the second radius may greater than the first radius by a distance of at least 2 millimeters or by at least 5 millimeters. in some embodiments, the ratio of the first radius of curvature to the second radius of curvature is in the range of 0.50 to 0.99. For example, the ratio of the first radius of curvature to the second radius of curvature may be in the range of 0.90 to 0.99.

Additionally, in some embodiments, the condyle surface may contact the bearing surface at a third contact point on the condyle surface at a third degree of flexion. The third degree of flexion may be greater than the second degree of flexion and less than about 90 degrees. The condyle surface in the sagittal plane may have a third radius of curvature at the third contact point. The third radius of curvature may be greater than the first radius of curvature and less than the second radius of curvature. For example, in some embodiments, the third radius is greater than the second radius by at least 0.5 millimeters. However, in other embodiments, the third radius of curvature may be greater than the first and second radii of curvature.

In some embodiments, the condyle surface of the femoral component is a medial condyle surface and the bearing surface of the tibial bearing is a medial bearing surface. The femoral component may include a lateral condyle surface curved in the sagittal plane. The tibial bearing may include a lateral bearing surface configured to articulate with the lateral condyle surface of the femoral component. In some embodiments, the lateral condyle surface and the medial condyle surface are substantially symmetrical in the sagittal plane. However, in other embodiments, the lateral condyle surface and the medial condyle surface are not substantially symmetrical in the sagittal plane.

Additionally, in some embodiments, the lateral condyle surface may contact the lateral bearing surface at a first point on the lateral condyle surface at a third degree of flexion. The third degree of flexion may be less than about 30 degrees. The lateral condyle surface may also contact the lateral bearing surface at a second point on the lateral condyle surface at a fourth degree of flexion. The fourth degree of flexion may be greater than the third degree of flexion. Additionally, the lateral condyle surface in the sagittal plane may include a first radius of curvature at the first contact point and a second radius of curvature at the second contact point. The second radius of curvature may be greater than the first radius of curvature by at least 0.5 millimeters. In some embodiments, the second radius of curvature of the lateral condyle may be different from the second radius of curvature of the medial condyle. Additionally, in some embodiments, the second degree of flexion may be different from the fourth degree of flexion. Further, in some embodiments, the difference between the first radius of curvature and the second radius of curvature is different from the difference between the third radius of curvature and the fourth radius of curvature.

According to another aspect, and orthopaedic knee prosthesis may include a femoral component and a tibial bearing. The femoral component may include a condyle surface curved in the sagittal plane. The tibial bearing may include a bearing surface configured to articulate with the condyle surface of the femoral component. The condyle surface may contact the bearing surface at a first contact point on the condyle surface at a first degree of flexion. The first degree of flexion may be less than 30 degrees. The condyle surface may also contact the bearing surface at a second contact point on the condyle surface at a second degree of flexion. The second degree of flexion may be greater than about 30 degrees.

In such embodiments, the condyle surface in the sagittal plane has a first radius of curvature at the first contact point and a second radius of curvature at the second contact point. The ratio of the first radius of curvature to the second radius of curvature may be in the range of 0.80 to 0.99. For example, the ratio of the first radius of curvature to the second radius of curvature may be in the range of 0.90 to 0.99.

According to a further aspect, an orthopaedic knee prosthesis may include a femoral component and a tibial bearing. The femoral component may include a condyle surface curved in the sagittal plane. The tibial bearing may include a bearing surface configured to articulate with the condyle surface of the femoral component. The condyle surface may contact the bearing surface at a first contact point on the condyle surface at a first degree of flexion. The first degree of flexion may be, for example, about 0 degrees. The condyle surface may also contact the bearing surface at a second contact point on the condyle surface at a second degree of flexion. The second degree of flexion may be greater than about 50 degrees. For example, in some embodiments, the second degree of flexion may be greater than about 70 degrees.

In some embodiments, the condyle surface in the sagittal plane may include a curved surface section extending from the first contact point to the second contact point. The curved surface section may be defined by a substantially constant radius of curvature.

According to yet another aspect, an orthopaedic knee prosthesis may include a femoral component. The femoral component may include a condyle surface curved in the sagittal plane. The condyle surface may include an anterior surface and a posterior surface. The anterior surface and the posterior surface may meet at an inferior-most point on the condyle surface. The posterior surface may include a superior-most point and a mid-point located equidistance from the superior-most point and the inferior-most point. The posterior surface in the sagittal plane may have a first radius of curvature at a first point on the posterior surface between the inferior-most point and the mid-point. The posterior surface in the sagittal plane may have a second radius of curvature at a second point on the posterior surface between the first point and the superior-most point. The second radius of curvature may be greater than the first radius of curvature by at least 0.5 millimeters.

BRIEF DESCRIPTION OF THE DRAWINGS

The detailed description particularly refers to the following figures, in which:

FIG. 2 is an exploded perspective view of another embodiment of an orthopaedic knee prosthesis;

DETAILED DESCRIPTION OF THE DRAWINGS

Figure 1:
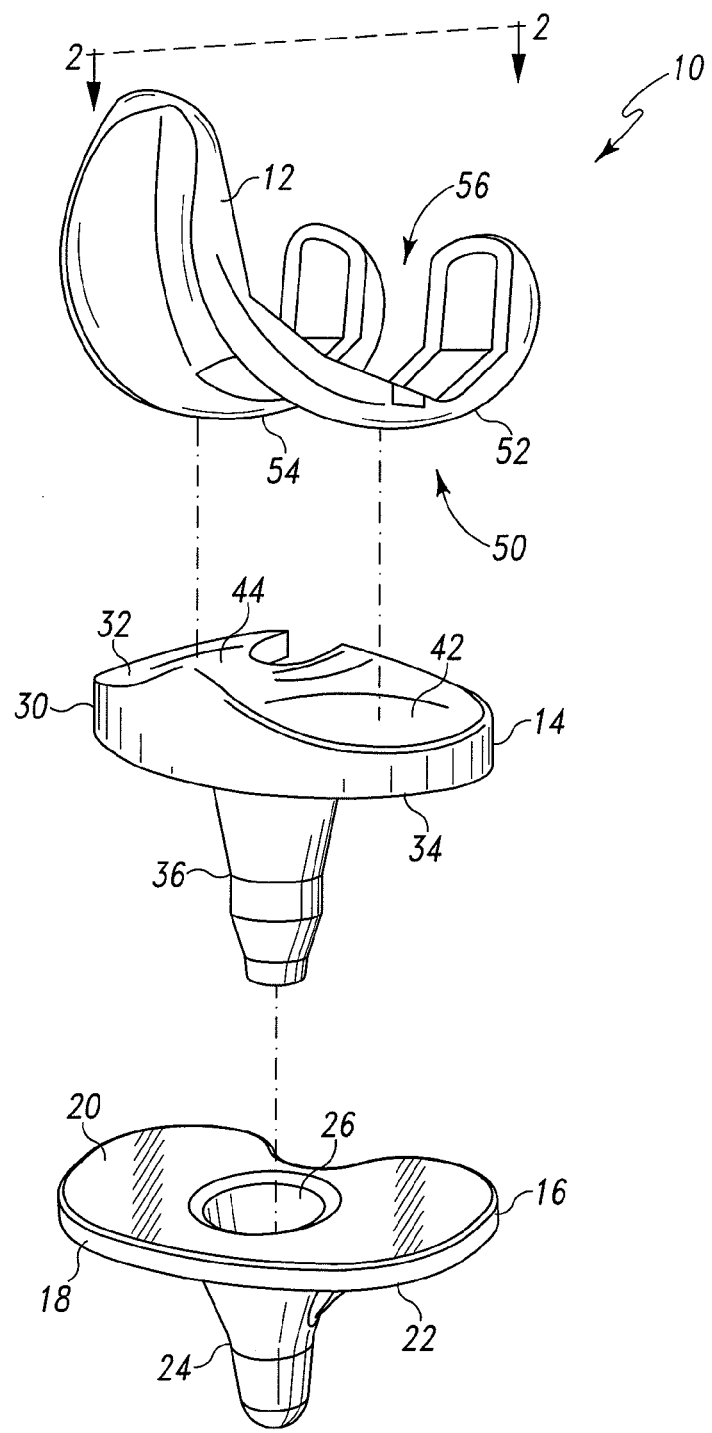
FIG. 1 is an exploded perspective view of one embodiment of an orthopaedic knee prosthesis.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIG. 1, in one embodiment, an orthopaedic knee prosthesis 10 includes a femoral component 12, a tibial bearing 14, and a tibial tray 16. The femoral component 12 and the tibial tray 16 are illustratively formed from a metallic material such as cobalt-chromium or titanium, but may be formed from other materials, such as a ceramic material, a polymer material, a bio-engineered material, or the like, in other embodiments. The tibial bearing 14 is illustratively formed from a polymer material such as a ultra-high molecular weight polyethylene (UHMWPE), but may be formed from other materials, such as a ceramic material, a metallic material, a bio-engineered material, or the like, in other embodiments.

As discussed in more detail below, the femoral component 12 is configured to articulate with the tibial bearing 14, which is configured to be coupled with the tibial tray 16. In the illustrative embodiment of FIG. 1, the tibial bearing 14 is embodied as a rotating or mobile tibial bearing and is configured to rotate relative to the tibial tray 12 during use. However, in other embodiments, the tibial bearing 14 may be embodied as a fixed tibial bearing, which may be limited or restricted from rotating relative the tibial tray 16.

The tibial tray 16 is configured to be secured to a surgically-prepared proximal end of a patient's tibia (not shown). The tibial tray 16 may be secured to the patient's tibia via use of bone adhesive or other attachment means. The tibial tray 16 includes a platform 18 having a top surface 20 and a bottom surface 22. Illustratively, the top surface 20 is generally planar and, in some embodiments, may be highly polished. The tibial tray 16 also includes a stem 24 extending downwardly from the bottom surface 22 of the platform 18. A cavity or bore 26 is defined in the top surface 20 of the platform 18 and extends downwardly into the stem 24. The bore 26 is formed to receive a complimentary stem of the tibial insert 14 as discussed in more detail below.

As discussed above, the tibial bearing 14 is configured to be coupled with the tibial tray 16. The tibial bearing 14 includes a platform 30 having an upper bearing surface 32 and a bottom surface 34. In the illustrative embodiment wherein the tibial bearing 14 is embodied as a rotating or mobile tibial bearing, the bearing 14 includes a stem 36 extending downwardly from the bottom surface 32 of the platform 30. When the tibial bearing 14 is coupled to the tibial tray 16, the stem 36 is received in the bore 26 of the tibial tray 16. In use, the tibial bearing 14 is configured to rotate about an axis defined by the stem 36 relative to the tibial tray 16. In embodiments wherein the tibial bearing 14 is embodied as a fixed tibial bearing, the bearing 14 may or may not include the stem 22 and/or may include other devices or features to secure the tibial bearing 14 to the tibial tray 12 in a non-rotating configuration.

The upper bearing surface 32 of the tibial bearing 14 includes a medial bearing surface 42 and a lateral bearing surface 44. The medial and lateral bearing surfaces 42, 44 are configured to receive or otherwise contact corresponding medial and lateral condyles of the femoral component 14 as discussed in more detail below. As such, each of the bearing surface 42, 44 has a concave contour.

The femoral component 12 is configured to be coupled to a surgically-prepared surface of the distal end of a patient's femur (not shown). The femoral component 12 may be secured to the patient's femur via use of bone adhesive or other attachment means. The femoral component 12 includes an outer, articulating surface 50 having a pair of medial and lateral condyles 52, 54. The condyles 52, 54 are spaced apart to define an intracondyle opening 56 therebetween. In use, the condyles 52, 54 replace the natural condyles of the patient's femur and are configured to articulate on the corresponding bearing surfaces 42, 44 of the platform 30 of the tibial bearing 14.

The illustrative orthopaedic knee prosthesis 10 of FIG. 1 is embodied as a posterior cruciate-retaining knee prosthesis. That is, the femoral component 12 is embodied as a posterior cruciate-retaining knee prosthesis and the tibial bearing 14 is embodied as a posterior cruciate-retaining tibial bearing 14. However, in other embodiments, the orthopaedic knee prosthesis 10 may be embodied as a posterior cruciate-sacrificing knee prosthesis as illustrated in FIG. 2.

In such embodiments, the tibial bearing 14 is embodied as posterior stabilizing tibial bearing and includes a spine 60 extending upwardly from the platform 30. The spine 60 is positioned between the bearing surfaces 42, 44 and includes an anterior side 62 and a posterior side 64 having a cam surface 66. In the illustrative embodiment, the cam surface 66 has a substantially concave curvature. However, spines 60 including cam surfaces 66 having other geometries may be used in other embodiments. For example, a tibial bearing including a spine having a substantially "S"-shaped cross-sectional profile, such as the tibial bearing described in U.S. patent application Ser. No. 12/165,582, entitled "Posterior Stabilized Orthopaedic Prosthesis" and now issued as U.S. Pat. No. 8,206,451 by Joseph G. Wyss, et al., which is hereby incorporated by reference, may be used in other embodiments.

Additionally, in such embodiments, the femoral component 12 is embodied as a posterior stabilized femoral component and includes an intracondyle notch or recess 57 (rather than an opening 56). A posterior cam 80 (shown in phantom) and an anterior cam 82 are positioned in the intracondyle notch 57. The posterior cam 80 is located toward the posterior side of the femoral component 12 and includes a cam surface 86 configured to engage or otherwise contact the cam surface 66 of the spine 60 of the tibial bearing 12 during.

It should be appreciated that although the orthopaedic knee prosthesis 10 may be embodied as either a posterior cruciate-retaining or cruciate-sacrificing knee prosthesis, the femoral component 12 and the tibial bearing 14 of the knee prosthesis 10 are discussed below, and illustrated in the remaining figures, in regard to a posterior cruciate-retaining knee prosthesis with the understanding that such description is equally applicable to those embodiments wherein orthopaedic knee prosthesis 10 is embodied as a posterior cruciate-sacrificing (posterior stabilized) orthopaedic knee prosthesis.

It should be appreciated that the illustrative orthopaedic knee prosthesis 10 is configured to replace a patient's right knee and, as such, the bearing surface 42 and the condyle 52 are referred to as being medially located; and the bearing surface 44 and the condyle 54 are referred to as being laterally located. However, in other embodiments, the orthopaedic knee prosthesis 10 may be configured to replace a patient's left knee. In such embodiments, it should be appreciated that the bearing surface 42 and the condyle 52 may be laterally located and the bearing surface 44 and the condyle 54 may be medially located. Regardless, the features and concepts described herein may be incorporated in an orthopaedic knee prosthesis configured to replace either knee joint of a patient.

Figure 3:
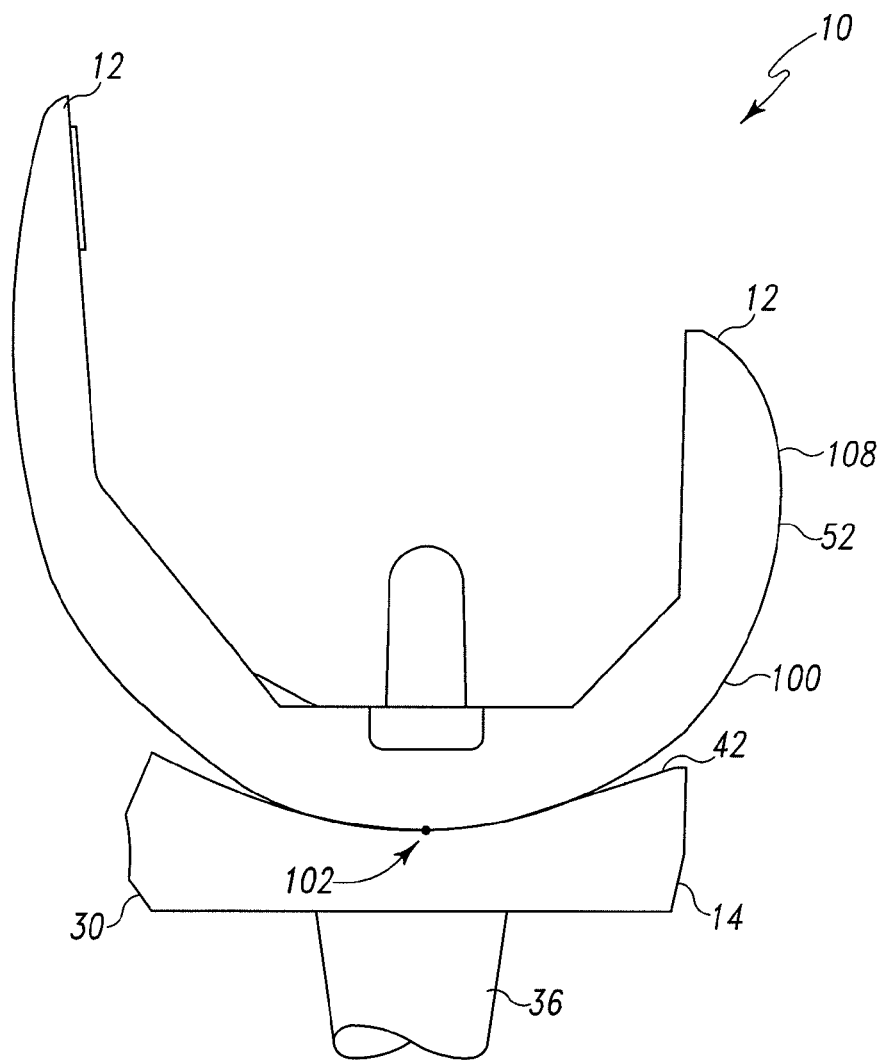
FIG. 3 is a cross-section view of one embodiment of a femoral component and tibial bearing of FIG. 1 taken generally along section lines 2-2 and having the femoral component articulated to a first degree of flexion.
Figure 4:
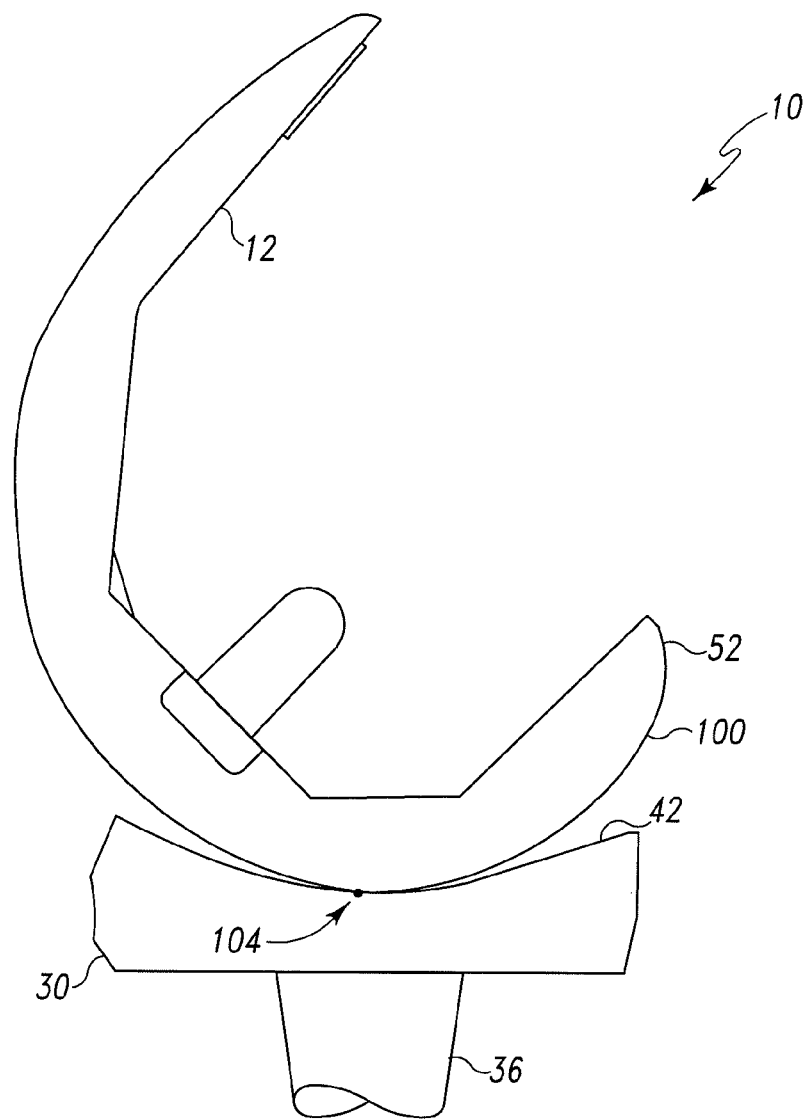
FIG. 4 is a cross-sectional view of a femoral component and tibial bearing of FIG. 3 having the femoral component articulated to a second degree of flexion.
Figure 5:
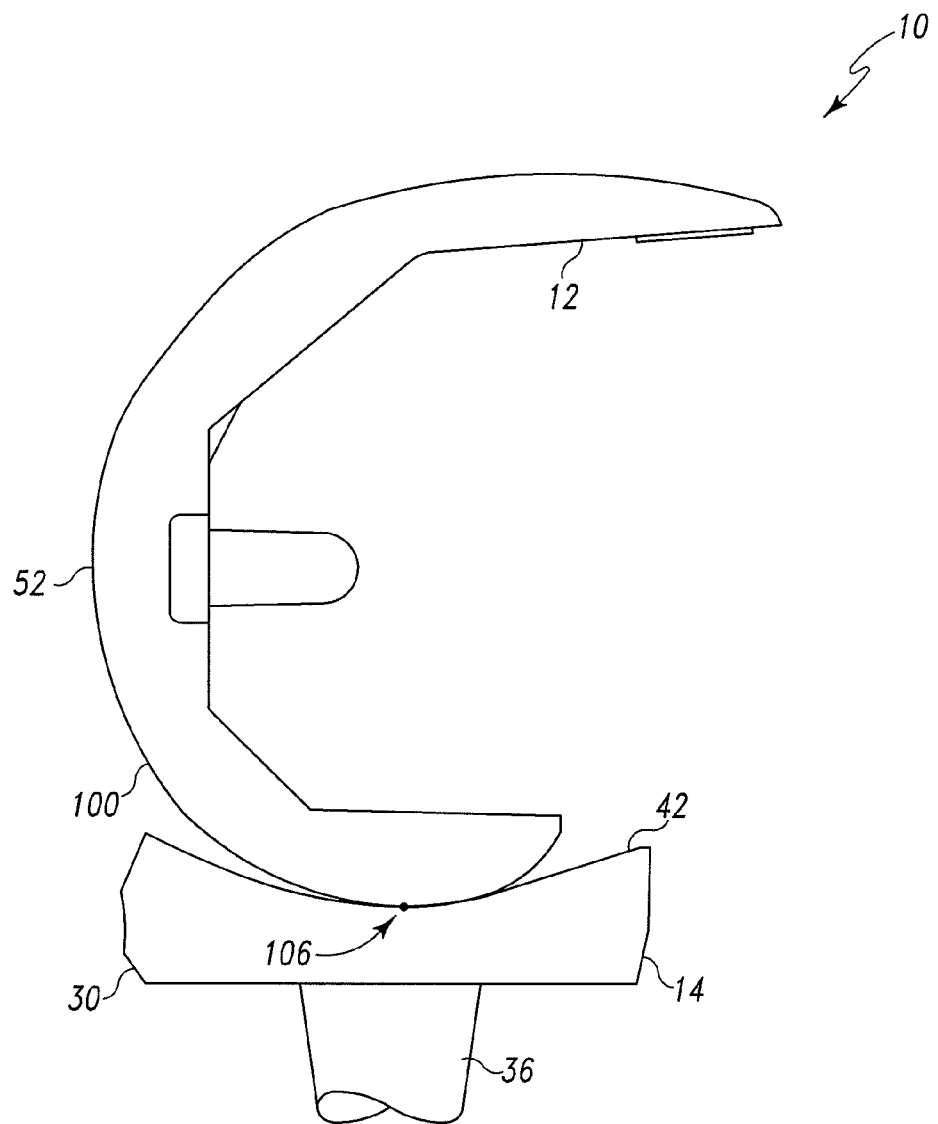
FIG. 5 is a cross-sectional view of a femoral component and tibial bearing of FIG. 3 having the femoral component articulated to a third degree of flexion.

Referring now to FIGS. 3-5, the femoral component 12 is configured to articulate on the tibial bearing 14 during use. Each condyle 52, 54 of the femoral component 12 includes a condyle surface 100, which is convexly curved in the sagittal plane and configured to contact the respective bearing surface 42, 44. For example, in one embodiment as shown in FIG. 3, when the orthopaedic knee prosthesis 10 is in extension or is otherwise not in flexion (e.g., a flexion of about 0 degrees), the condyle surface 100 of the condyle 52 contacts the bearing surface 42 (or bearing surface 44 in regard to condyle 54) at one or more contact points 102 on the condyle surface 100.

Additionally, as the orthopaedic knee prosthesis 10 is articulated through the middle degrees of flexion, the femoral component 12 contacts the tibial bearing 14 at one or more contact points on the condyle surface 100. For example, in one embodiment as illustrated in FIG. 4, when the orthopaedic knee prosthesis 10 is articulated to a middle degree of flexion (e.g., at about 45 degrees), the condyle surface 100 contacts the bearing surface 42 at one or more contact points 104 on the condyle surface 100. Similarly, as the orthopaedic knee prosthesis 10 is articulated to a late degree of flexion (e.g., at about 70 degrees of flexion), the condyle surface 100 contacts the bearing surface 42 at one or more contact points 106 on the condyle surface 100 as illustrated in FIG. 5. It should be appreciated, of course, that the femoral component 12 may contact the tibial bearing 14 at a plurality of contact points on the condyle surface 100 at any one particular degree of flexion. However, for clarity of description, only the contact points 102, 104, 106 have been illustrated in FIGS. 3-5, respectively.

The orthopaedic knee prosthesis 10 is configured such that the amount of paradoxical anterior translation of the femoral component 12 relative to the tibial bearing 14 may be reduced or otherwise delayed to a later (i.e., larger) degree of flexion. In particular, as discussed in more detail below, the condyle surface 100 of one or both of the condyles 52, 54 has particular geometry or curvature configured to reduce and/or delay anterior translations and, in some embodiments, promote "roll-back" or posterior translation, of the femoral component 12. It should be appreciated that by delaying the onset of paradoxical anterior translation of the femoral component 12 to a larger degree of flexion, the overall occurrence of paradoxical anterior translation may be reduced during those activities of a patient in which deep flexion is not typically obtained.

In a typical orthopaedic knee prosthesis, paradoxical anterior translation may occur whenever the knee prosthesis is positioned at a degree of flexion greater than zero degrees. The likelihood of anterior translation generally increases as the orthopaedic knee prosthesis is articulated to larger degrees of flexion, particularly in the mid-flexion range. In such orientations, paradoxical anterior translation of the femoral component on the tibial bearing can occur whenever the tangential (traction) force between the femoral component and the tibial bearing fails to satisfy the following equation:

$$T < \mu N \qquad (1)$$

wherein "T" is the tangential (traction) force, "$\mu$" is the coefficient of friction of the femoral component and the tibial bearing, and "N" is the normal force between the femoral component and the tibial bearing. As a generalization, the tangential (traction) force between the femoral component and the tibial bearing can be defined as $$T = M/R \qquad (2)$$

wherein "T" is the tangential (traction) force between the femoral component and the tibial bearing, "M" is the knee moment, and "R" is the radius of curvature in the sagittal plane of the condyle surface in contact with the tibial bearing at the particular degree of flexion. It should be appreciated that equation (2) is a simplification of the governing real-world equations, which does not consider such other factors as inertia and acceleration. Regardless, the equation (2) provides insight that paradoxical anterior translation of an orthopaedic knee prosthesis may be reduced or delayed by controlling the radius of curvature of the condyle surface of the femoral component. That is, by controlling the radius of curvature of the condyle surface (e.g., increasing or maintaining the radius of curvature), the right-hand side of equation (2) may be reduced, thereby decreasing the value of the tangential (traction) force and satisfying the equation (1). As discussed above, by ensuring that the tangential (traction) force satisfies equation (1), paradoxical anterior translation of the femoral component on the tibial bearing may be reduced or otherwise delayed to a greater degree of flexion.

Based on the above analysis, to reduce or delay the onset of paradoxical anterior translation, the geometry of the condyle surface 100 of one or both of the condyles 52, 54 of the femoral component 12 is controlled. For example, in some embodiments, the radius of curvature of the condyle surface 100 is controlled such that the radius of curvature is held constant over a range of degrees of flexion and/or is increased in the early to mid flexion ranges. Comparatively, typical femoral components have decreasing radii of curvatures beginning at the distal radius of curvature (i.e., at about 0 degrees of flexion). However, it has been determined that by maintaining a relatively constant radius of curvature (i.e., not decreasing the radius of curvature) over a predetermined range of degrees of early to mid-flexion and/or increasing the radius of curvature over the predetermined range of degrees of flexion may reduce or delay paradoxical anterior translation of the femoral component 12. Additionally, in some embodiments, the rate of change in the radius of curvature of the condyle surface in the early to mid flexion ranges (e.g., from about 0 degrees to about 90 degrees) is controlled such that the rate of change is less than a predetermined threshold. That is, it has been determined that if the rate of decrease of the radius of curvature of the condyle surface 100 is greater than the predetermined threshold, paradoxical anterior translation may occur.

Figure 6:
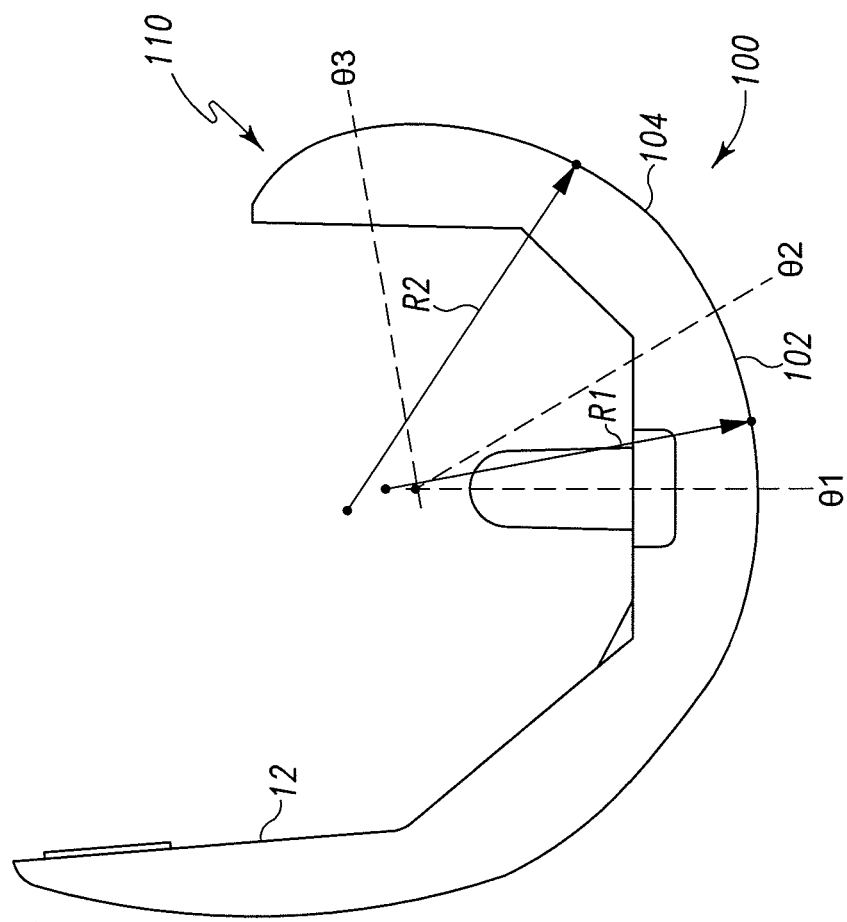
FIG. 6 is a cross-sectional view of one embodiment of the femoral component of FIG. 1.
Figure 7:
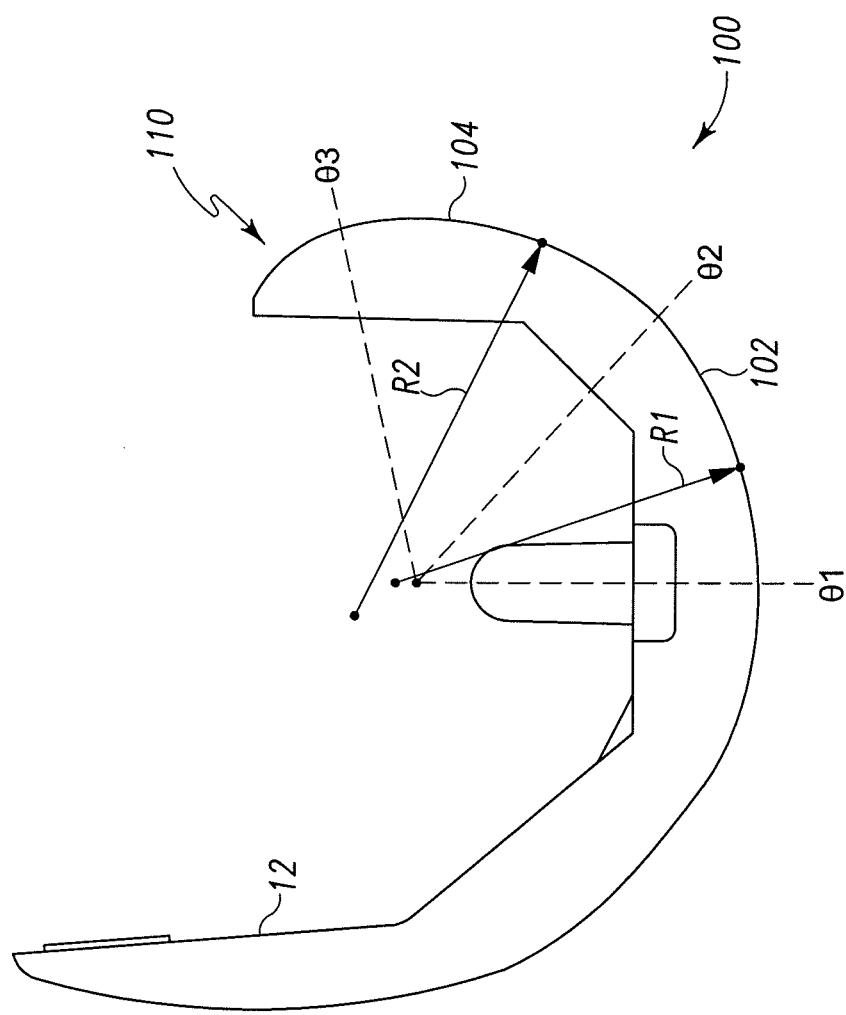
FIG. 7 is a cross-sectional view of another embodiment of the femoral component of FIG. 1.
Figure 8:
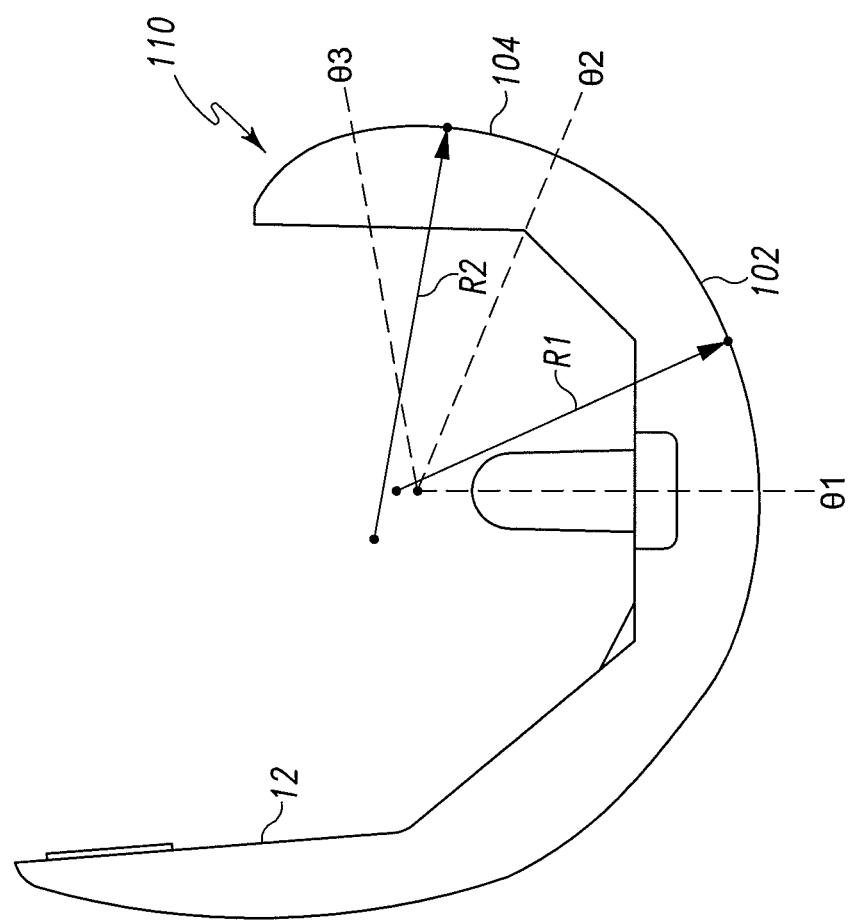
FIG. 8 is a cross-sectional view of another embodiment of the femoral component of FIG. 1.

Accordingly, in some embodiments as illustrated in FIGS. 6-8, the condyle surface 100 of the femoral component 12 has an increased radius of curvature in early to middle degrees of flexion from a smaller radius of curvature R1 to a larger radius of curvature R2. By increasing the radius of curvature, paradoxical anterior translation may be reduced or delayed to a later degree of flexion as discussed in more detail below.

The amount of increase between the radius of curvature R2 and the radius of curvature R3, as well as, the degree of flexion on the condyle surface 100 at which such increase occurs has been determined to affect the occurrence of paradoxical anterior translation. Multiple simulations of various femoral component designs were performed using the LifeMOD/Knee Sim, version 1007.1.0 Beta 16 software program, which is commercially available from LifeModeler, Inc. of San Clemente, Calif., to analyze the effect of increasing the radius of curvature of the condyle surface of the femoral components in early and mid flexion. Based on such analysis, it has been determined that paradoxical anterior translation of the femoral component relative to the tibial bearing may be reduced or otherwise delayed by increasing the radius of curvature of the condyle surface by an amount in the range of about 0.5 millimeters to about 5 millimeters or more at a degree of flexion in the range of about 30 degrees of flexion to about 90 degrees of flexion.

Figure 10:
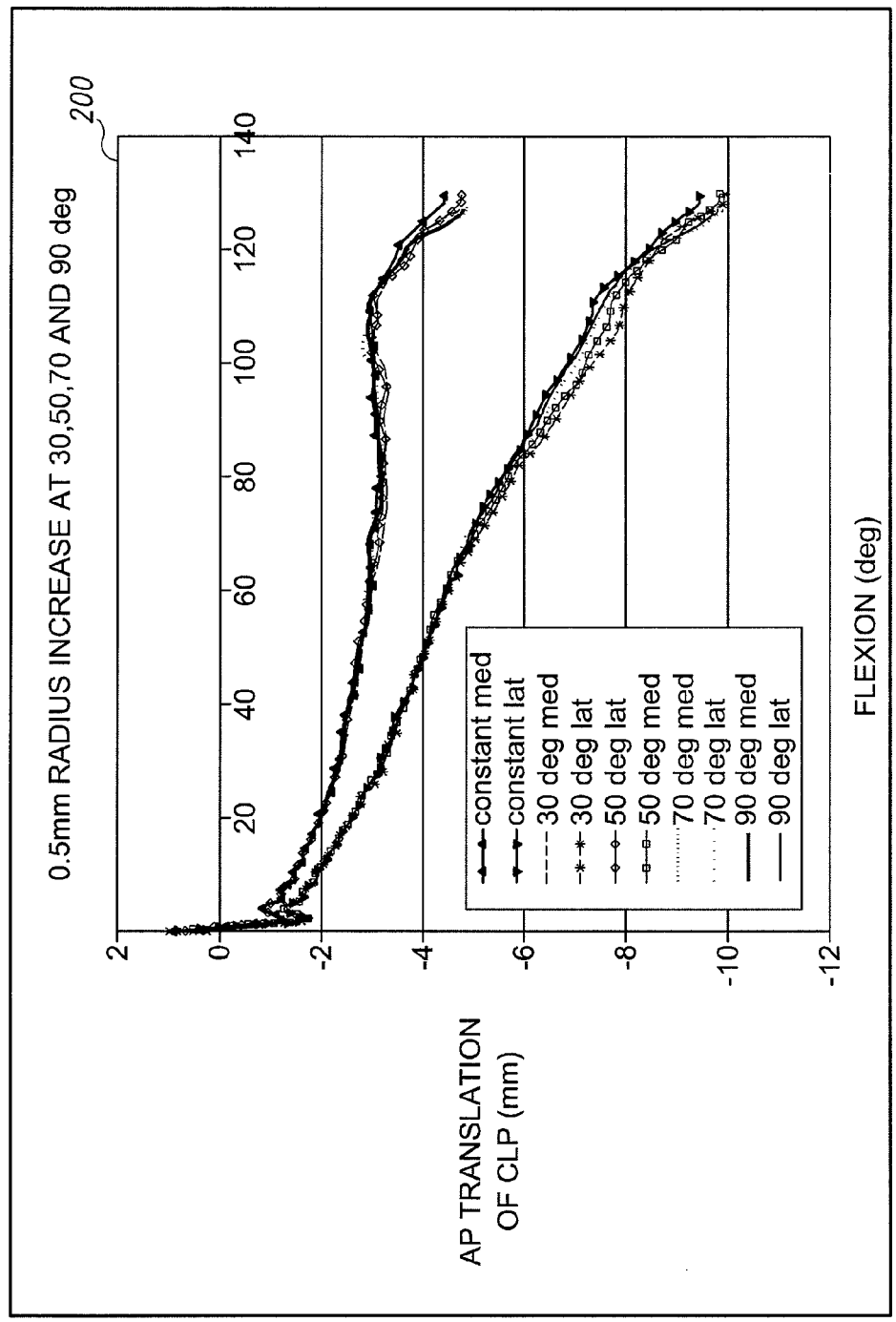
FIG. 10 is a graph of the anterior-posterior translation of a simulated femoral component having an increased radius of curvature located at various degrees of flexion.
Figure 11:
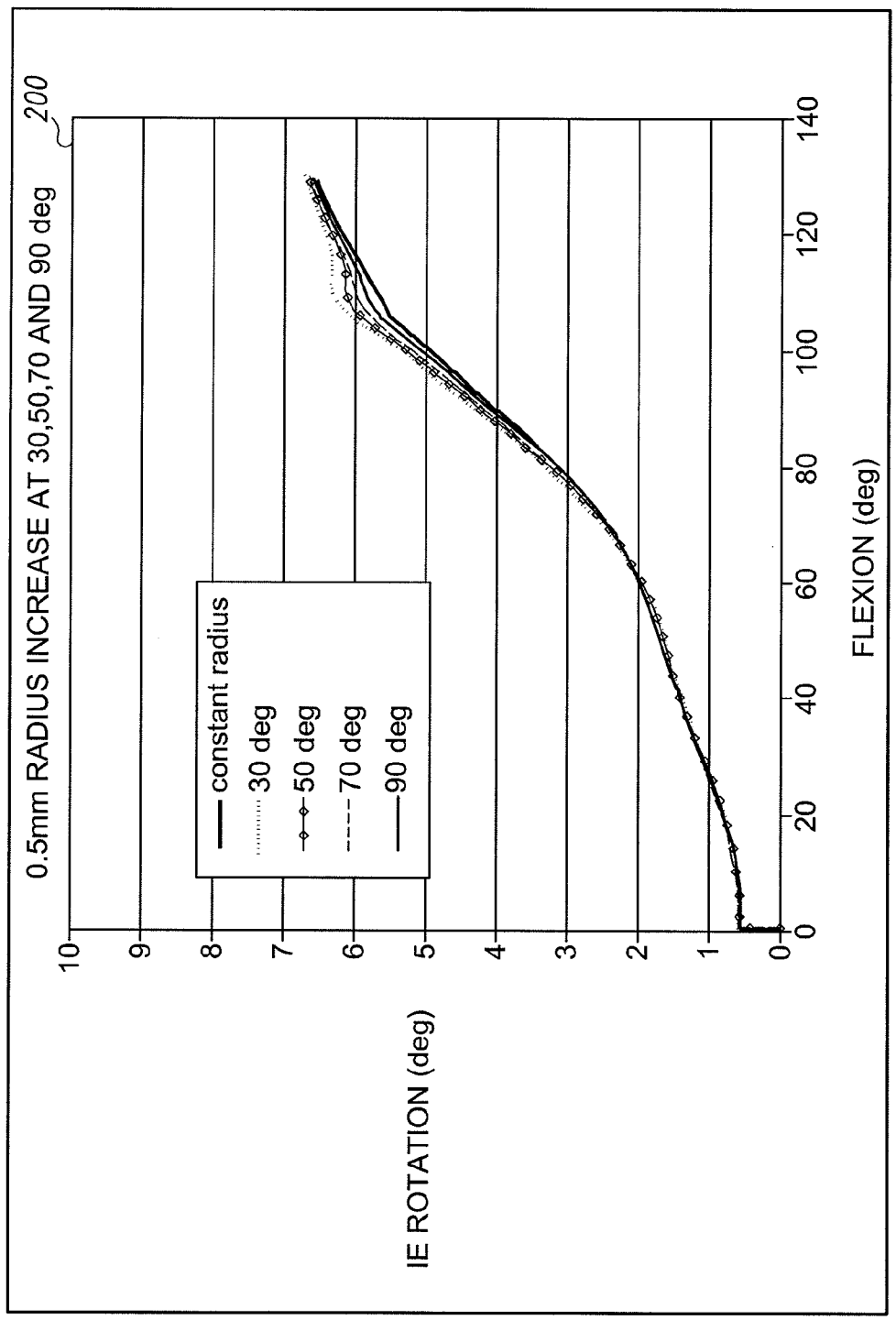
FIG. 11 is a graph of the internal rotation (as indicated by an upward or positive direction in the graph) of a simulated tibial insert with respect to the simulated femoral component of FIG. 10.
Figure 12:
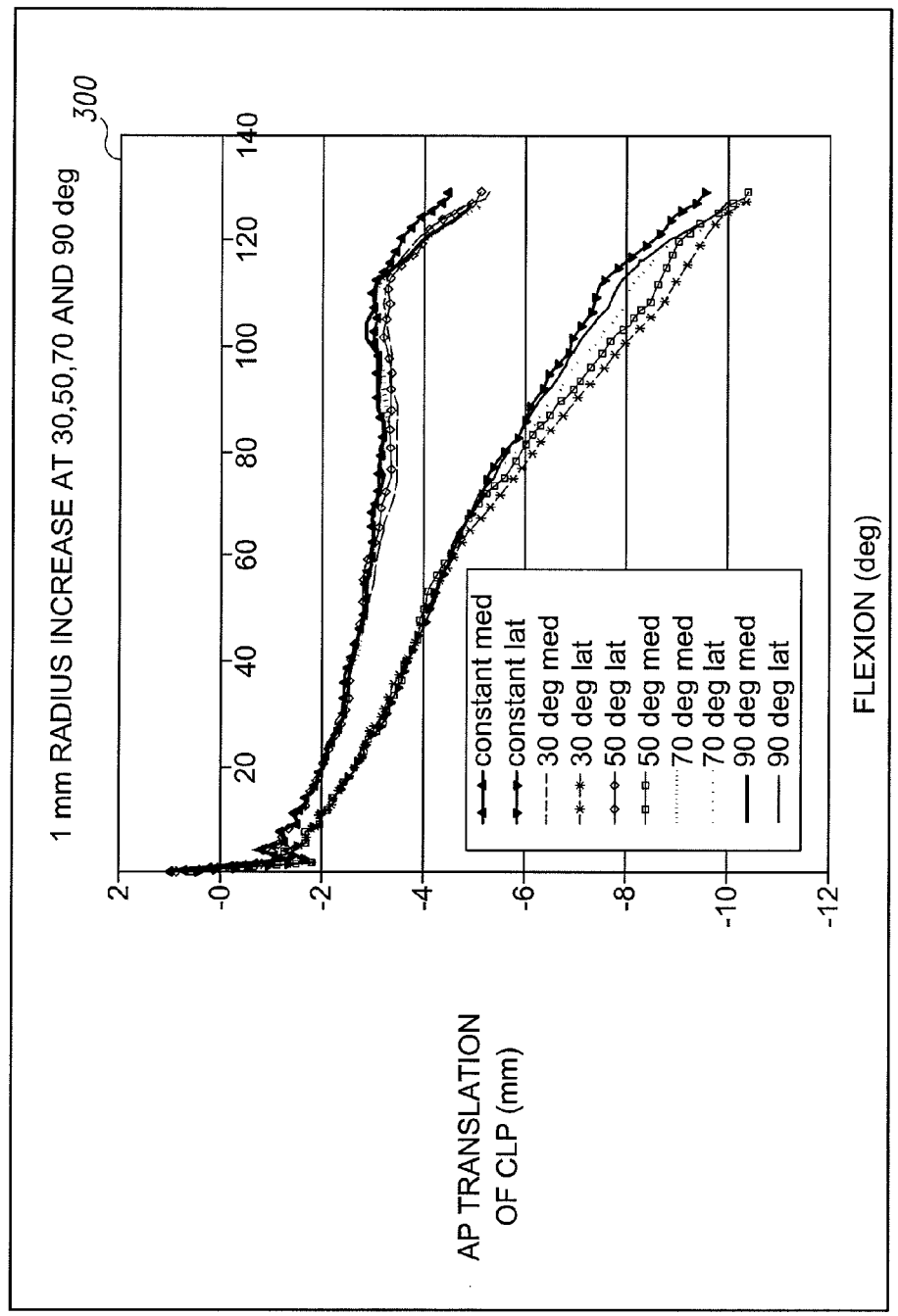
FIG. 12 is a graph of the anterior-posterior translation of another simulated femoral component having an increased radius of curvature located at various degrees of flexion.
Figure 13:
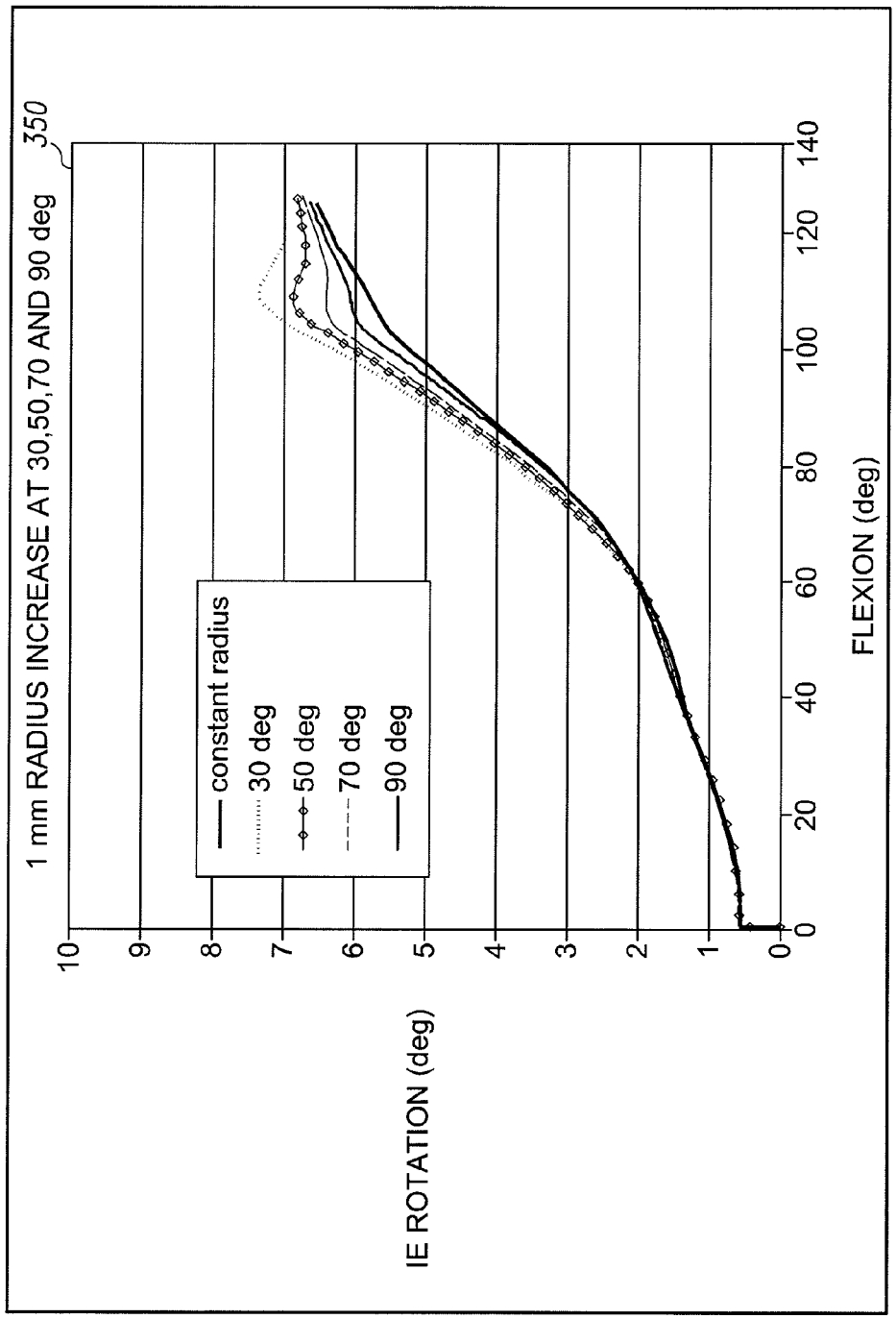
FIG. 13 is a graph of the internal rotation (as indicated by an upward or positive direction in the graph) of a simulated tibial insert with respect to the simulated femoral component of FIG. 12.

For example, the graphs 200, 250 illustrated in FIGS. 10 and 11 present the results of a deep bending knee simulation using a femoral component wherein the radius of curvature of the condyle surface is increased by 0.5 millimeters (i.e., from 25.0 millimeters to 25.5 millimeters) at 30 degrees of flexion, at 50 degrees of flexion, at 70 degrees of flexion, and at 90 degrees of flexion. Similarly, the graphs 300, 350 illustrated in FIGS. 12 and 13 present the results of a deep bending knee simulation using a femoral component wherein the radius of curvature of the condyle surface is increased by 1.0 millimeters (i.e., from 25.0 millimeters to 26.0 millimeters) at 30 degrees of flexion, at 50 degrees of flexion, at 70 degrees of flexion, and at 90 degrees of flexion.

Figure 14:
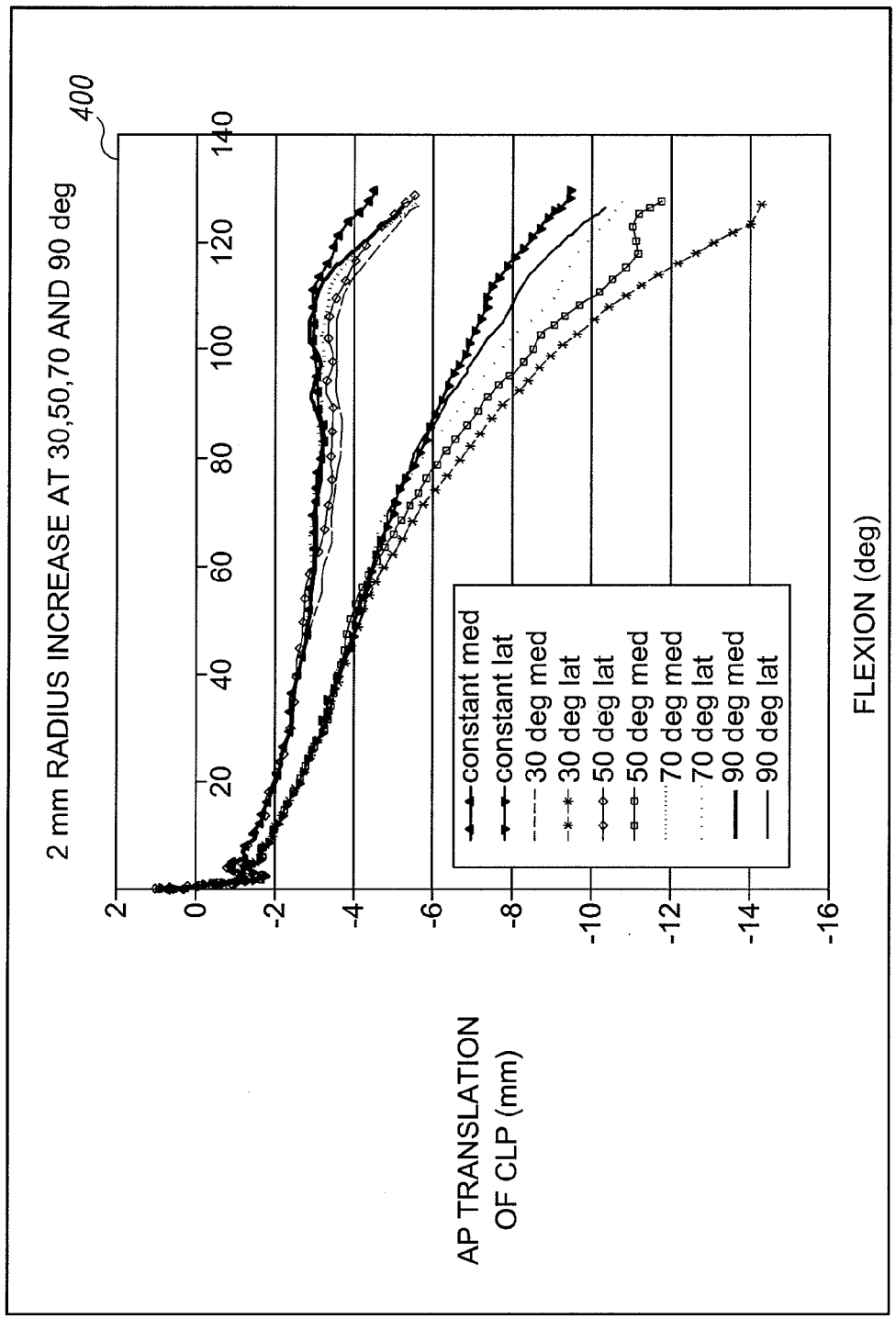
FIG. 14 is a graph of the anterior-posterior translation of another simulated femoral component having an increased radius of curvature located at various degrees of flexion.
Figure 15:
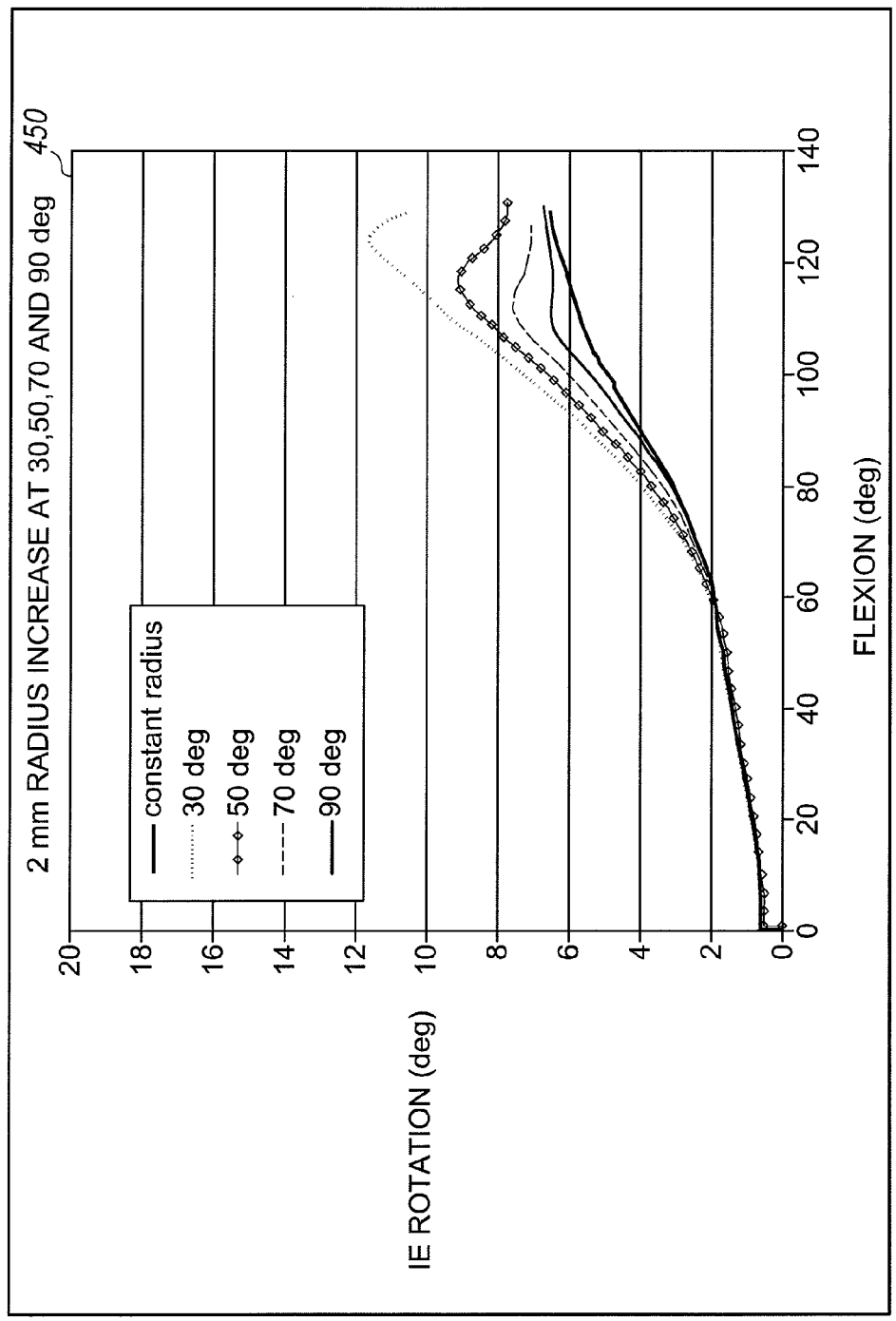
FIG. 15 is a graph of the internal rotation (as indicated by an upward or positive direction in the graph) of a simulated tibial insert with respect to the simulated femoral component of FIG. 14.
Figure 16:
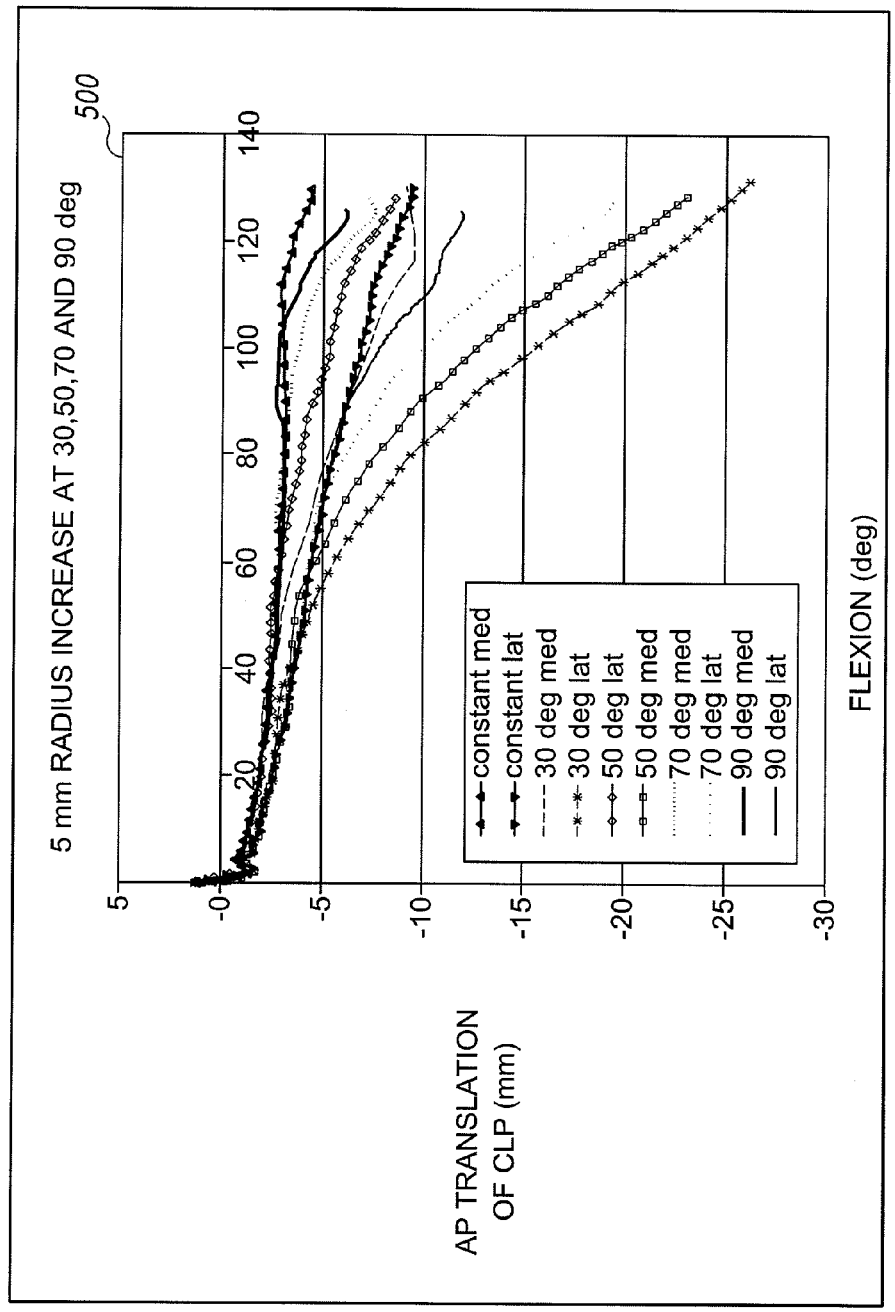
FIG. 16 is a graph of the anterior-posterior translation of another simulated femoral component having an increased radius of curvature located at various degrees of flexion.
Figure 17:
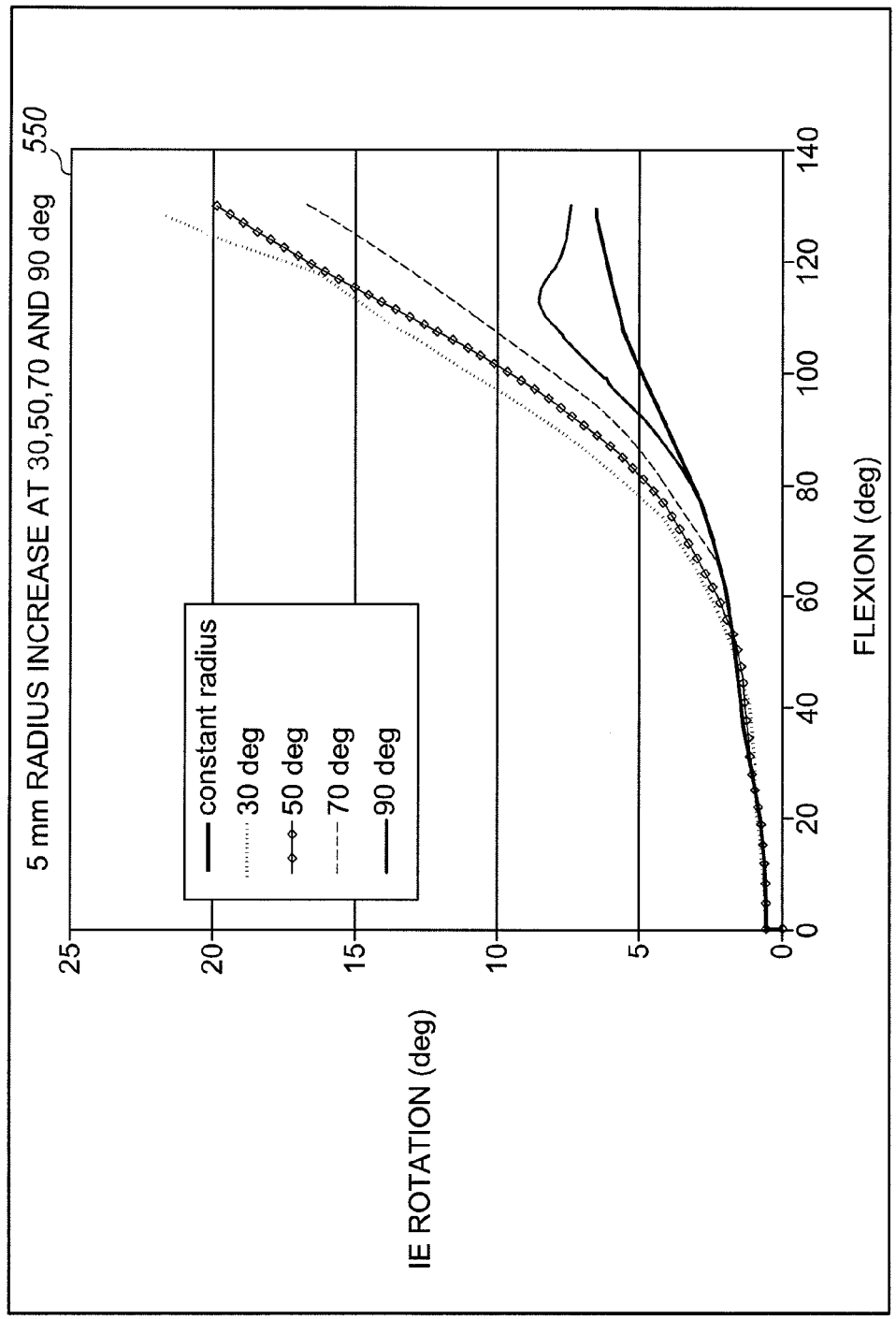
FIG. 17 is a graph of the internal rotation (as indicated by an upward or positive direction in the graph) of a simulated tibial insert with respect to the simulated femoral component of FIG. 16.

The graphs 400 and 450 illustrated in FIGS. 14 and 15 present the results of a deep bending knee simulation using a femoral component wherein the radius of curvature of the condyle surface is increased by 2.0 millimeters (i.e., from 25.0 millimeters to 27.0 millimeters) at 30 degrees of flexion, at 50 degrees of flexion, at 70 degrees of flexion, and at 90 degrees of flexion. Additionally, the graphs 500, 550 illustrated in FIGS. 16 and 17 present the results of a deep bending knee simulation using a femoral component wherein the radius of curvature of the condyle surface is increased by 5.0 millimeters (i.e., from 25.0 millimeters to 26.0 millimeters) at 30 degrees of flexion, at 50 degrees of flexion, at 70 degrees of flexion, and at 90 degrees of flexion.

In the graphs 200, 300, 400, 500, the condylar lowest or most distal points (CLP) of the medial condyle ("med") and the lateral condyle ("lat") of the femoral component are graphed as a representation of the relative positioning of the femoral component to the tibial bearing. As such, a downwardly sloped line represents roll-back of the femoral component on the tibial bearing and an upwardly sloped line represents anterior translation of the femoral component on the tibial bearing. In the graphs 250, 350, 450, 550, the amount of relative internal-external rotation in degrees between the simulated femoral component and tibial bearing for each illustrative embodiment are graphed with respect to each degree of flexion. An upwardly sloped line in graphs 250, 350, 450, 550 corresponds to an amount of internal rotation of the tibia with respect to the femur (or external rotation of the femur with respect to the tibia).

As illustrated in the graphs 200, 300, 400, 500, anterior sliding of the femoral component was delayed until after about 100 degrees of flexion in each of the embodiments; and the amount of anterior translation was limited to less than about 1 millimeter. In particular, "roll-back" of the femoral component on the tibial bearing was promoted by larger increases in the radius of curvature of the condyle surface at earlier degrees of flexion. Additionally, as illustrated in graphs 250, 350, 450, 550, internal-external rotation between the femoral component and tibial bearing was increased by larger increases in the radius of curvature of the condyle surface at earlier degrees of flexion. Of course, amount of increase in the radius of curvature and the degree of flexion at which such increase is introduced is limited by other factors such as the anatomical joint space of the patient's knee, the size of the tibial bearing, and the like. Regardless, based on the simulations reported in the graphs 200, 250, 300, 350, 400, 450, 500, 550, paradoxical anterior translation of the femoral component on the tibial bearing can be reduced or otherwise delayed by increasing the radius of curvature of the condyle surface of the femoral component during early to mid flexion.

Accordingly, referring back to FIGS. 6-9, the condyle surface 100 in the sagittal plane is formed in part from a number of curved surface sections 102, 104 in one embodiment. The sagittal ends of each curved surface section 102, 204 are tangent to the sagittal ends of any adjacent curved surface section of the condyles surface 100. Each curved surface section 102, 104 is defined by a respective radius of curvature. In particular, the curved surface section 102 is defined by a radius of curvature R1 and the curved surface section 104 is defined by a radius of curvature R2.

As discussed above, the condyle surface 100 of the femoral component 12 is configured such that the radius of curvature R2 of the curved surface section 104 is greater than the radius of curvature R1 of the curved surface section 102. In one embodiment, the radius of curvature R2 is greater than the radius of curvature R1 by 0.5 millimeters or more. In another embodiment, the radius of curvature R2 is greater than the radius of curvature R1 by 1 millimeters or more. Additionally in another embodiment, the radius of curvature R2 is greater than the radius of curvature R1 by 2 millimeters or more. In a particular embodiment, the radius of curvature R2 is greater than the radius of curvature R3 by a distance in the range of about 0.5 millimeters to about 5 millimeters.

It should be appreciated, however, that the particular increase of radius of curvature between R1 and R2 may be based on or scaled to the particular size of the femoral component 12 in some embodiments. For example, in some embodiments, the increase of the radius of curvature between R1 and R2 may be based on the size of R1. That is, the ratio of the radius of curvature R1 to the radius of curvature R2 may be below a predetermined threshold or within a specified range of a target value in some embodiments. For example, in some embodiments, the ratio of the radius of curvature R1 to the radius of curvature R2 is between 0.80 and 0.99. In one particular embodiment, the ratio of the radius of curvature R1 to the radius of curvature R2 is between 0.90 and 0.99.

Each of the curved surface sections 102, 104 contacts the bearing surface 42 (or 44) of the tibial bearing 14 through different ranges of degrees of flexion. For example, the curved surface section 102 extends from an earlier degree of flexion θ1 to a later degree of flexion θ2. The curved surface section 104 extends from the degree of flexion θ2 to a later degree of flexion θ3. The particular degrees of flexion θ1, θ2, and θ3, may vary between embodiments and be based on criteria such as the type of orthopaedic prosthesis (e.g., cruciate retaining or posterior stabilized), positioning of other component of the orthopaedic prosthesis (e.g., the positioning of a cam of the femoral component 12), the size of the femoral cam, the curvature of the tibial bearing 14, the anatomy of a patient, etc. For example, in one embodiment, as illustrated in FIG. 6, the curved surface section 102 extends from a degree of flexion θ1 of about 0 degrees of flexion to a degree of flexion θ2 of about 30 degrees of flexion. The curved surface section 104 extends from the degree of flexion θ2 of about 30 degrees of flexion to a degree of flexion θ3 of about 110 degrees of flexion.

As discussed above, the particular degrees of flexion θ1, θ2, θ3 may be determined based on the particular embodiment and other features of the femoral component 12. For example, the larger degree of flexion θ3 may be determined or otherwise based on the desire to allow the most posterior-superior end 110 of the femoral component 12 to "wrap" around. Such a configuration may properly size or configure the femoral component 12 for positioning within the joint gap of a patient. The end 110 of the femoral component 12 may be formed from a number of additional radii of curvatures, which begin at the degree of flexion θ3. As such, the particular degree of flexion θ3 may be determined or based on the degree of flexion at which the additional radii of curvatures must begin to form the end 110 as desired.

Figure 9:
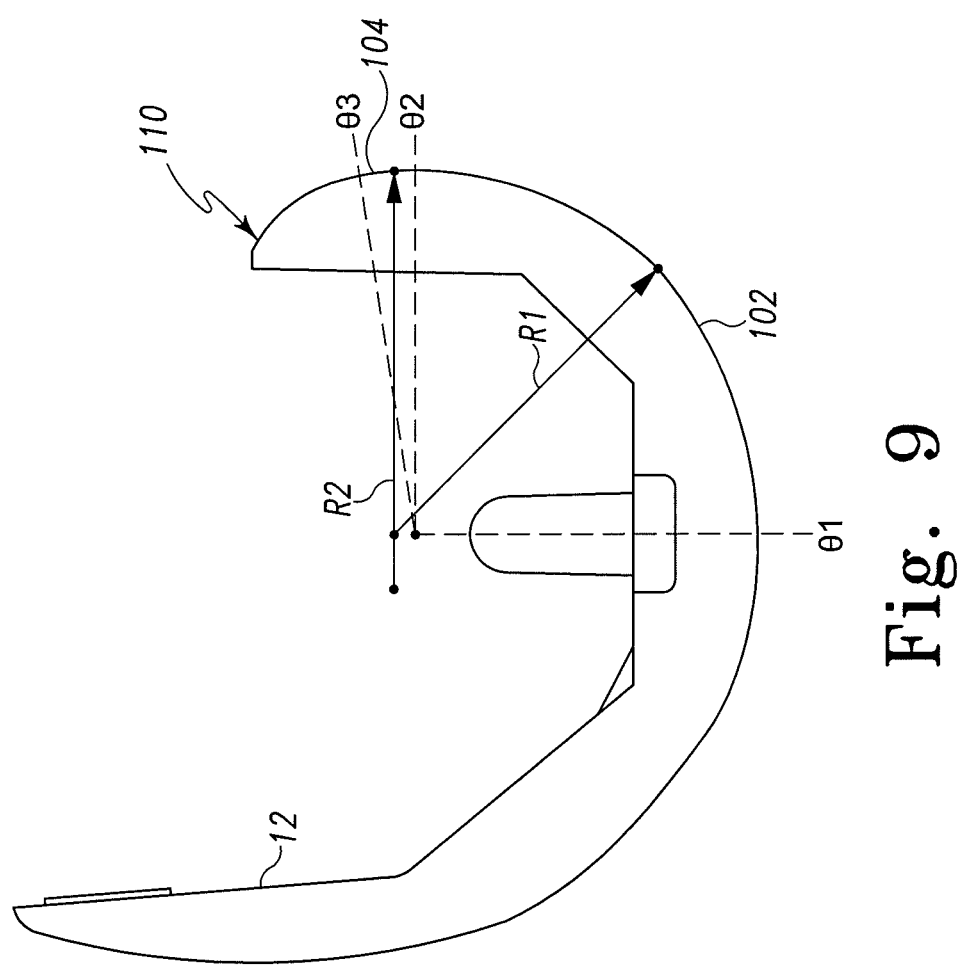
FIG. 9 is a cross-sectional view of another embodiment of the femoral component of FIG. 1.

In another embodiment, as illustrated in FIG. 7, the curved surface section 102 extends from a degree of flexion θ1 of about 0 degrees of flexion to a degree of flexion θ2 of about 50 degrees of flexion. The curved surface section 104 extends from the degree of flexion θ2 of about 50 degrees of flexion to a degree of flexion θ3 of about 110 degrees of flexion. Additionally, in another embodiment, as illustrated in FIG. 8, the curved surface section 102 extends from a degree of flexion θ1 of about 0 degrees of flexion to a degree of flexion θ2 of about 70 degrees of flexion. The curved surface section 104 extends from the degree of flexion θ2 of about 70 degrees of flexion to a degree of flexion θ3 of about 110 degrees of flexion. In another illustrative embodiment, as illustrated in FIG. 9, the curved surface section 102 extends from a degree of flexion θ1 of about 0 degrees of flexion to a degree of flexion θ2 of about 90 degrees of flexion. The curved surface section 104 extends from the degree of flexion θ2 of about 90 degrees of flexion to a degree of flexion θ3 of about 110 degrees of flexion.

Again, it should be appreciated that the embodiments of FIGS. 6-9 are illustrative embodiments and, in other embodiments, each of the curved surface sections 102, 104 may extend from degrees of flexion different from those shown and discussed above in regard to FIGS. 6-9. For example, in each of the embodiments of FIGS. 6-9, although the curved surface section 102 is illustrated as beginning at about 0 degrees of flexion, the curved surface section 102 may begin at a degree of flexion prior to 0 degrees of flexion (i.e., a degree of hyperextension) in other embodiments.

Figure 18:
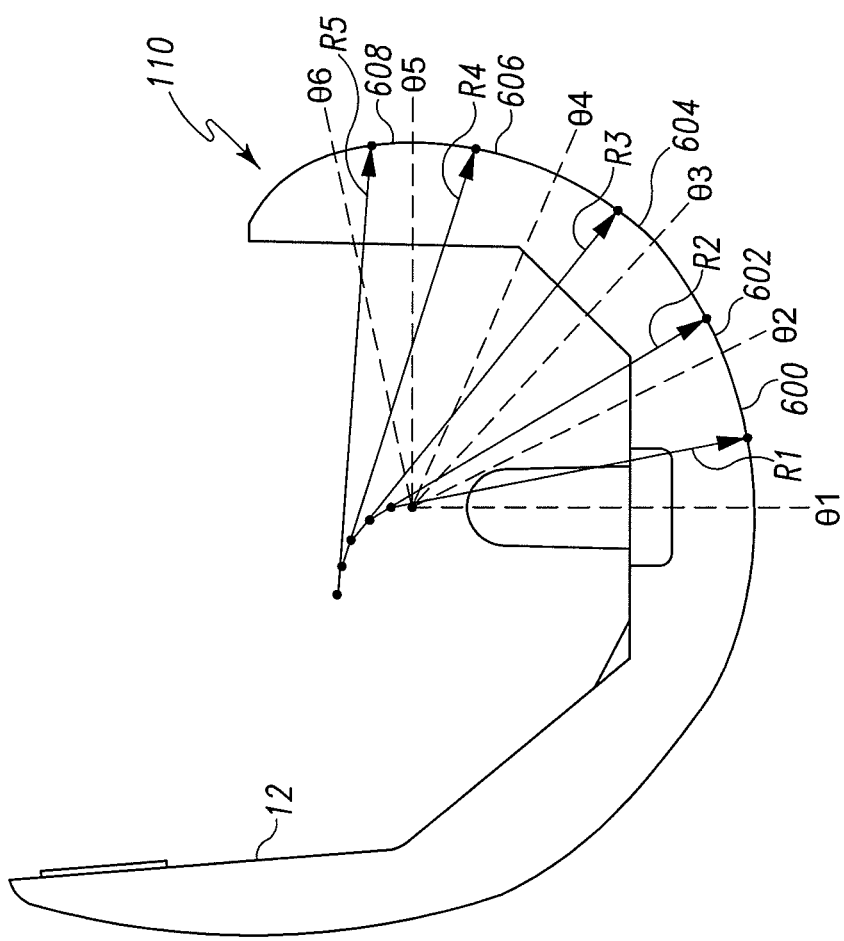
FIG. 18 is a cross-sectional view of another embodiment of the femoral component of FIG. 1.

Referring now to FIG. 18, it should be appreciated that although the illustrative embodiments of FIGS. 6-9 include only one increase of radius of curvature (i.e., between R1 and R2), the condyle surface may include any number of increases in radius of curvature in other embodiments. For example, in one embodiment as shown in FIG. 18, the condyle surface 100 may be formed from a number of curved surface sections 600, 602, 604, 606, 608, the sagittal ends of each of which are tangent to adjacent curved surface sections. The curved surface section 600 extends from an earlier degree of flexion θ1 to a later degree of flexion θ2. The curved surface section 602 extends from the degree of flexion θ2 to a later degree of flexion θ3. The curved surface section 604 extends from the degree of flexion θ3 to a later degree of flexion θ4. The curved surface section 606 extends from the degree of flexion θ4 to a later degree of flexion θ5. The curved surface section 608 extends from the degree of flexion θ5 to a later degree of flexion θ6.

Each of the curved surface sections 600, 602, 604, 606, 608 is defined by a respective radius of curvature. In particular, the curved surface section 600 is defined by a radius of curvature R1, the curved surface section 602 is defined by a radius of curvature R2, the curved surface section 604 is defined by a radius of curvature R3, the curved surface section 606 is defined by a radius of curvature R4, and the curved surface section 607 is defined by a radius of curvature R5. The radius of curvature R2 is greater than the radius of curvature R1. Similarly, the radius of curvature R3 is greater than the radius of curvature R2. The radius of curvature R4 is greater than the radius of curvature R3. And, the radius of curvature R5 is greater than the radius of curvature R4. In this way, the condyle surface 100 is formed from a plurality of curved surface sections, each having a radius of curvature greater than the adjacent anterior curved surface section. Again, the embodiment illustrated in FIG. 18 is just one illustrative embodiment. In other embodiments, the condyle surface 100 may be formed from a greater or lesser number of curved surface sections having an increased radius of curvature relative to an anteriorly adjacent curved surface section.

Figure 19:
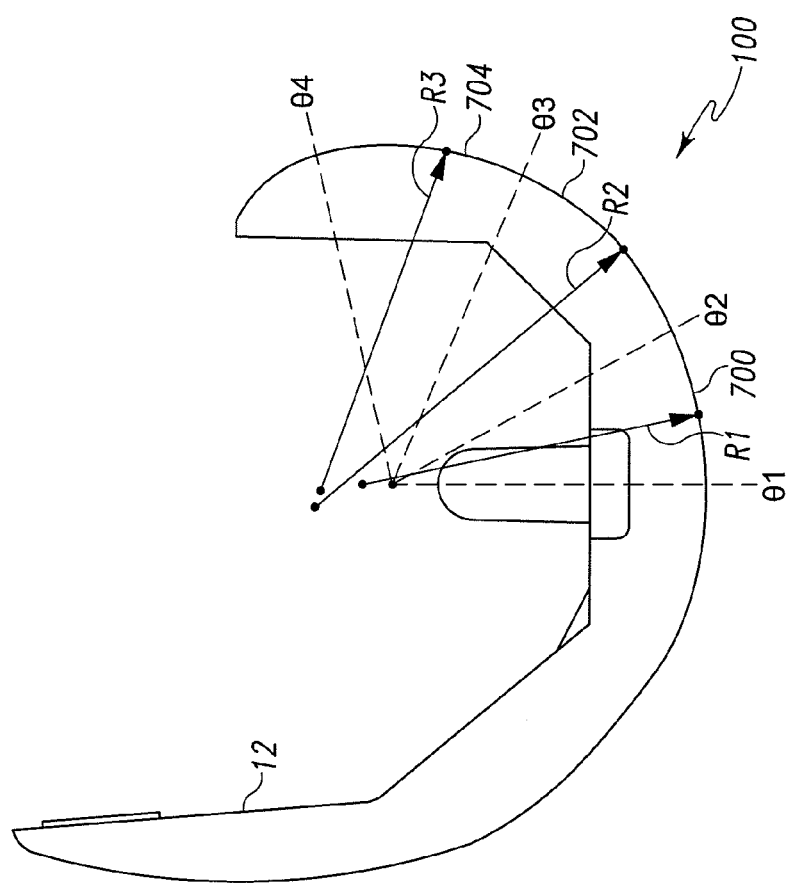
FIG. 19 is a cross-sectional view of another embodiment of the femoral component of FIG. 1.

Referring now to FIG. 19, the condyle surface 100 may include an increase in radius of curvature and a decrease in radius of curvature in the early to middle degrees of flexion. That is, in some embodiments, the radius of curvature of the condyle surface 100 may initially increase from an initial radius of curvature to an increased radius of curvature and subsequently decrease to a decreased radius of curvature that is larger than the initial radius prior to late flexion (e.g., prior to about 90 degrees of flexion).

For example, in one embodiment shown in FIG. 19, the condyle surface 100 be formed from a number of curved surface sections 700, 702, 704, the sagittal ends of each of which are tangent to adjacent curved surface sections. The curved surface section 700 extends from an earlier degree of flexion θ1 to a later degree of flexion θ2. The curved surface section 72 extends from the degree of flexion θ2 to a later degree of flexion θ3. The curved surface section 704 extends from the degree of flexion θ3 to a later degree of flexion θ4.

Each of the curved surface sections 700, 702, 704 is defined by a respective radius of curvature. In particular, the curved surface section 700 is defined by a radius of curvature R1, the curved surface section 6702 is defined by a radius of curvature R2, and the curved surface section 704 is defined by a radius of curvature R3. The radius of curvature R2 is greater than the radius of curvature R1. The radius of curvature R3 is less than the radius of curvature R2 and greater than the radius of curvature R1. In this way, the radius of curvature of the condyle surface 100 initially increases from R1 to R2 and subsequently decreases to R3. However, because R3 is still greater than the distal radius R1, paradoxical anterior translation of the femoral component 12 may be reduced or delayed as discussed in detail above.

Additionally, as discussed above, the particular amount of increase between R1 and R2 and between R1 and R3 may vary between embodiments and be based on one or more of a number of various criteria such as, for example, the type of orthopaedic prosthesis (e.g., cruciate retaining or posterior stabilized), positioning of other component of the orthopaedic prosthesis (e.g., the positioning of a cam of the femoral component 12), the size of the femoral cam, the curvature of the tibial bearing 14, the anatomy of a patient, etc. In one particular embodiment, each of the radius of curvature R2, R3 is greater than the radius of curvature R1 by at least 0.5 millimeters.

Figure 20:
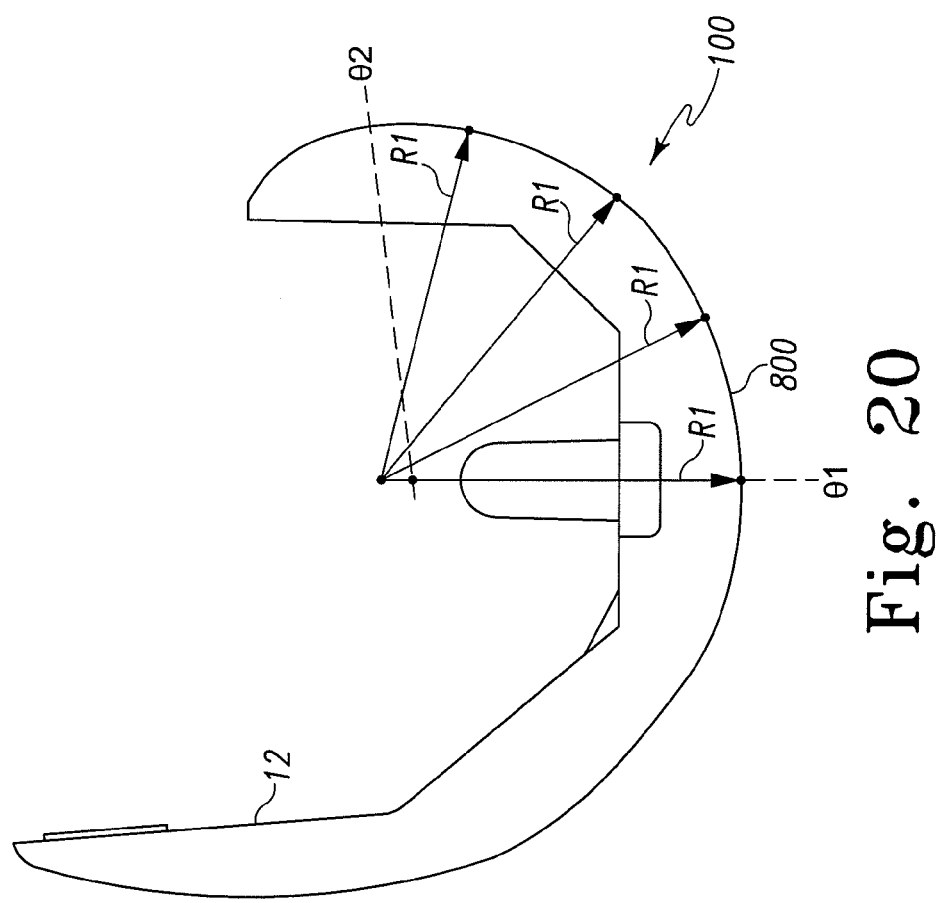
FIG. 20 is a cross-sectional view of another embodiment of the femoral component of FIG. 1.

Referring now to FIG. 20, another way to control the radius of curvature of the condyle surface 100 is to maintain the radius of curvature through early to middle degrees of flexion. As discussed above, typical femoral components have decreasing radii of curvatures beginning at the distal radius of curvature (i.e., at about 0 degrees of flexion). However, it has been determined that maintaining a relatively constant radius of curvature (i.e., not decreasing the radius of curvature) over a predetermined range of degrees of early to mid-flexion may reduce or delay paradoxical anterior translation of the femoral component 12.

Accordingly, in one embodiment as shown in FIG. 20, the condyle surface 100 may be formed from a curved surface section 800. The curved surface section 800 extends from an earlier degree of flexion θ1 to a later degree of flexion θ2. The curved surface section 800 is defined by a constant or substantially constant radius of curvature R1. In the illustrative embodiment, the curved surface section 800 subtends an angle of about 110 degrees, but may be larger or small in other embodiments. For example, in one particular embodiment, the curved surface section 800 subtends an angle of at least 50 degrees. Additionally, as discussed above, the particular degrees of flexion θ1, θ2 may be based on one or more of a number of various criteria such as, for example, the type of orthopaedic prosthesis (e.g., cruciate retaining or posterior stabilized), positioning of other component of the orthopaedic prosthesis (e.g., the positioning of a cam of the femoral component 12), the size of the femoral cam, the curvature of the tibial bearing 14, the anatomy of a patient, etc.

Figure 21:
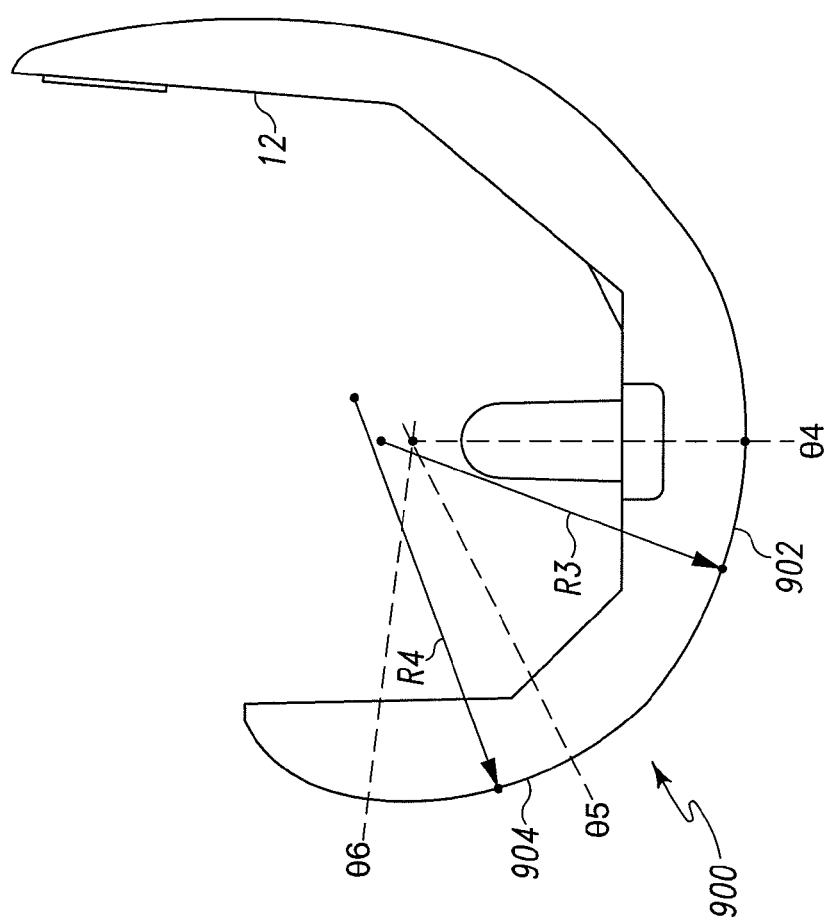
FIG. 21 is a cross-sectional view of another condyle of another embodiment of the femoral component of FIG. 1.

The overall shape and design of the condyle surface 100 of the femoral component 12 has been described above in regard to a single condyle 52, 54 of the femoral component 12. It should be appreciated that in some embodiments both condyles 52, 54 of the femoral component 12 may be symmetrical and have similar condyle surfaces 100. However, in other embodiments, the condyles 52, 54 of the femoral component 12 may asymmetrical. For example, as illustrated in FIG. 21, the femoral component 12 may include a second condyle 52, 54 having a condyle surface 900, which is defined in part by a plurality of curved surface sections 902, 904. The curved surface section 902 extends from an earlier degree of flexion θ4 to a later degree of flexion θ5. The curved surface section 904 extends from the degree of flexion θ5 to a later degree of flexion θ6. The curved surface section 902 is defined by a radius of curvature R3 and the curved surface section 904 is defined by a radius of curvature R4.

As such, in embodiments wherein the condyles 52, 54 are symmetrical, the degree of flexion θ4 is substantially equal to the degree of flexion θ1, the degree of flexion θ5 is substantially equal to the degree of flexion θ2, and the degree of flexion θ6 is substantially equal to the degree of flexion θ3. Additionally, the radius of curvature R3 is substantially equal to the radius of curvature R1 and the radius of curvature R4 is substantially equal to the radius of curvature R2.

However, in other embodiments, the condyles 52, 54 are asymmetrical. As such, the degree of flexion θ4 may be different from the degree of flexion θ1. Additionally or alternatively, the degree of flexion θ5 may be different from the degree of flexion θ2. That is, the increase in radius of curvature from R1 to R2 and from R3 to R4 may occur at different degrees of flexion between the condyles 52, 54. Further, the degree of flexion θ6 may be different from the degree of flexion θ3. Additionally, in those embodiments wherein the condyles 52, 54 are asymmetrical, the radius of curvature R3 may be different from the radius of curvature R1 and/or the radius of curvature R4 may be different from the radius of curvature R2.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the devices and assemblies described herein. It will be noted that alternative embodiments of the devices and assemblies of the present disclosure may not include all of the features described yet still benefit from at least some of the advantages of such features. Those of ordinary skill in the art may readily devise their own implementations of the devices and assemblies that incorporate one or more of the features of the present invention and fall within the spirit and scope of the present disclosure as defined by the appended claims.

The invention claimed is:

1. An orthopaedic knee prosthesis comprising:
   a femoral component having a condyle surface curved in the sagittal plane; and
   a tibial bearing having a bearing surface configured to articulate with the condyle surface of the femoral component,
   wherein the condyle surface (i) contacts the bearing surface at a first contact point on the condyle surface at a first degree of flexion, the first degree of flexion being in the range of 0 degrees to 10 degrees, (ii) contacts the bearing surface at a second contact point on the condyle surface at a second degree of flexion, the second degree of flexion being in the range of 10 degrees to 75 degrees, and (iii) contacts the bearing surface at a third contact point on the condyle surface at a third degree of flexion, the second degree of flexion being greater than the first degree of flexion and the third degree of flexion being greater than the second degree of flexion, wherein (i) the condyle surface in the sagittal plane has a first radius of curvature at the first contact point, a second radius of curvature at the second contact point, and a third radius of curvature at the third contact point, and (ii) the second radius of curvature is greater than the first radius of curvature and the third radius of curvature is less than the second radius of curvature, wherein the third radius of curvature is greater than the first radius of curvature by at least 0.5 millimeters, and wherein a curved surface section having a non-constant radius of curvature is defined between the first contact point and the third contact point.

2. The orthopaedic knee prosthesis of claim 1, wherein the second degree of flexion is about 30 degrees.

3. The orthopaedic knee prosthesis of claim 1, wherein the second radius of curvature is greater than the first radius of curvature by a distance of at least 2 millimeters.

4. The orthopaedic knee prosthesis of claim 3, wherein the second radius of curvature is greater than the first radius of curvature by a distance of at least 5 millimeters.

5. The orthopaedic knee prosthesis of claim 1, wherein the ratio of the first radius of curvature to the second radius of curvature is in the range of 0.50 to 0.99.

6. The orthopaedic knee prosthesis of claim 5, wherein the ratio of the first radius of curvature to the second radius of curvature is in the range of 0.90 to 0.99.

7. The orthopaedic knee prosthesis of claim 1,
wherein the third degree of flexion is greater than the second degree of flexion and less than about 90 degrees.

8. The orthopaedic knee prosthesis of claim 1, wherein:
(i) the condyle surface of the femoral component is a medial condyle surface and the bearing surface of the tibial bearing is a medial bearing surface,
(ii) the femoral component further includes a lateral condyle surface curved in the sagittal plane, and
(iii) the tibial bearing further includes a lateral bearing surface configured to articulate with the lateral condyle surface of the femoral component.

9. The orthopaedic knee prosthesis of claim 8, wherein the lateral condyle surface and the medial condyle surface are substantially symmetrical in the sagittal plane.

10. The orthopaedic knee prosthesis of claim 8,
wherein the lateral condyle surface (i) contacts the lateral bearing surface at a first contact point on the lateral condyle surface at a third degree of flexion, the third degree of flexion being less than about 30 degrees, and
(ii) contacts the lateral bearing surface at a second contact point on the lateral condyle surface at a fourth degree of flexion, the fourth degree of flexion being greater than the third degree of flexion, and
wherein (i) the lateral condyle surface in the sagittal plane has a first radius of curvature at the first contact point, (ii) the lateral condyle surface in the sagittal plane has a second radius of curvature at the second contact point, and (iii) the second radius of curvature of the lateral condyle is greater than the first radius of curvature of the lateral condyle by at least 0.5 millimeters.

11. The orthopaedic knee prosthesis of claim 10, wherein the second radius of curvature of the lateral condyle is different from the second radius of curvature of the medial condyle.

12. The orthopaedic knee prosthesis of claim 10, wherein the second degree of flexion is different from the fourth degree of flexion.

13. The orthopaedic knee prosthesis of claim 10, wherein a difference between the first radius of curvature and the second radius of curvature is different from a difference between the third radius of curvature and the fourth radius of curvature.

14. An orthopaedic knee prosthesis comprising:
a femoral component having a condyle surface curved in the sagittal plane; and
a tibial bearing having a bearing surface configured to articulate with the condyle surface of the femoral component,
wherein the condyle surface (i) contacts the bearing surface at a first contact point on the condyle surface at a first degree of flexion, the first degree of flexion being less than 30 degrees, (ii) contacts the bearing surface at a second contact point on the condyle surface at a second degree of flexion, the second degree of flexion being in the range of 30 degrees to 75 degrees, and (iii) contacts the bearing surface at a third contact point on the condyle surface at a third degree of flexion that is greater than the second degree of flexion,
wherein (i) the condyle surface in the sagittal plane has a first radius of curvature at the first contact point, (ii) the condyle surface in the sagittal plane has a second radius of curvature at the second contact point, (iii) the ratio of the first radius of curvature to the second radius of curvature is in the range of 0.80 to 0.99, and (iv) the condyle surface in the sagittal plane has a third radius of curvature at the third contact point that is less than the second radius of curvature,
wherein the third radius of curvature is greater than the first radius of curvature by at least 0.5 millimeters,
wherein a curved surface section having a non-constant radius of curvature is defined between the first contact point and the third contact point.

15. The orthopaedic knee prosthesis of claim 14, wherein the ratio of the first radius of curvature to the second radius of curvature is from 0.90 to 0.99.

* * * * *